(12) United States Patent
Goetsch et al.

(10) Patent No.: US 8,945,871 B2
(45) Date of Patent: Feb. 3, 2015

(54) ANTI-IGF-IR ANTIBODIES AND USES THEREOF

(71) Applicant: Pierre Fabre Medicament, Boulogne-Billancourt (FR)

(72) Inventors: Liliane Goetsch, Ayze (FR); Nathalie Corvaia, Collonges Sous Saleves (FR)

(73) Assignee: Pierre Fabre Medicament, Boulogne-Billancourt (FR)

( * ) Notice: Subject to any disclaimer, the term of this patent is extended or adjusted under 35 U.S.C. 154(b) by 0 days.

(21) Appl. No.: 13/745,142

(22) Filed: Jan. 18, 2013

(65) Prior Publication Data

US 2013/0125252 A1    May 16, 2013

Related U.S. Application Data

(62) Division of application No. 11/989,204, filed as application No. PCT/EP2006/064543 on Jul. 21, 2006, now Pat. No. 8,361,461.

(60) Provisional application No. 60/701,622, filed on Jul. 22, 2005.

(30) Foreign Application Priority Data

Jul. 22, 2005 (FR) ..................................... 05 07829

(51) Int. Cl.
| C07K 16/28 | (2006.01) |
| C07K 14/705 | (2006.01) |
| C07K 16/46 | (2006.01) |
| A61K 39/395 | (2006.01) |
| A61K 39/00 | (2006.01) |

(52) U.S. Cl.
CPC ....... *C07K 16/2863* (2013.01); *A61K 2039/505* (2013.01); *C07K 2316/96* (2013.01); *C07K 2317/24* (2013.01)
USPC .................... 435/69.1; 435/320.1; 435/252.3; 536/23.53

(58) Field of Classification Search
None
See application file for complete search history.

(56) References Cited

PUBLICATIONS

Rudikoff et al., Proc Natl Acad Sci USA, vol. 79 p. 1979, 1982.*
Colman et al., Research in Immunology, 145:33-36, 1994.*
Piatesi et al., ChemBio Chem 5: 460-466, 2004.*
MacCallum et al., Mol. Biol 262: 732-745, 1996.*
Pascalis et al., The Journal of Immunology 169: 3076-3084, 2002.*
Wu et al., J. Mol. Biol. 294: 151-162, 1999.*
Bendig et al., Methods: A Companion to Methods in Enzymology, 8:83-93, 1995.*

* cited by examiner

*Primary Examiner* — Phuong Huynh
(74) *Attorney, Agent, or Firm* — Birch, Stewart, Kolasch & Birch, LLP

(57) ABSTRACT

The present invention relates to novel antibodies capable of binding specifically to the human insulin-like growth factor I receptor (IGF-IR). The invention likewise comprises the use of these antibodies as a medicament for the prophylactic and/or therapeutic treatment of cancers overexpressing IGF-IR, stimulated either by IGF1 and/or IGF2, or any pathology connected with the overexpression of said receptor as well as in processes or kits for diagnosis of illnesses connected with the overexpression of the IGF-IR and/or the IGF-I/Insulin hybrid receptor.

5 Claims, 7 Drawing Sheets

Figure 1:
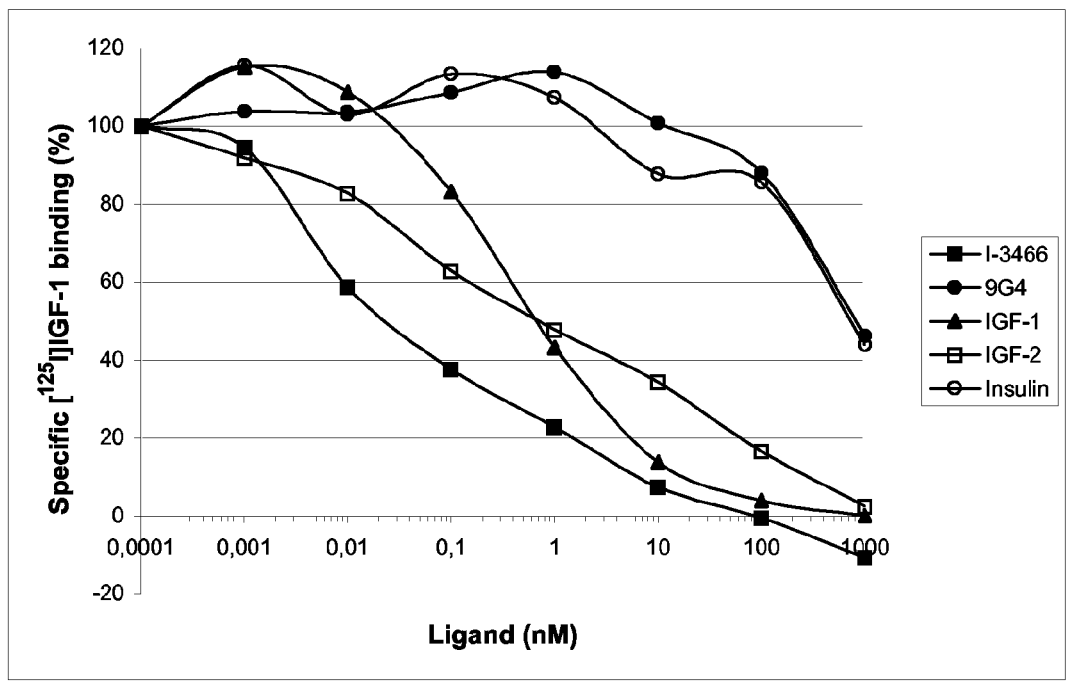

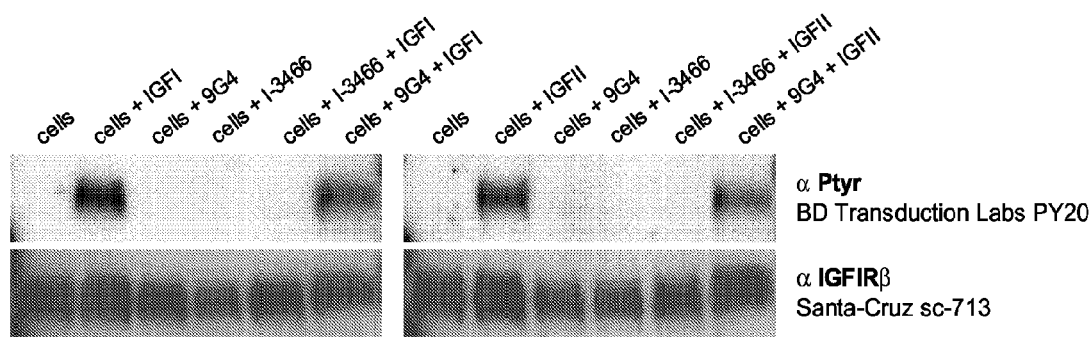
FIGURE 4A          FIGURE 4B
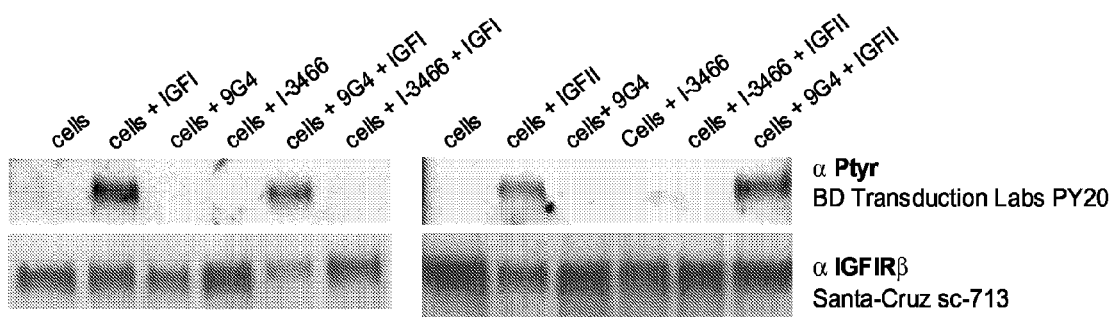
FIGURE 5A          FIGURE 5B

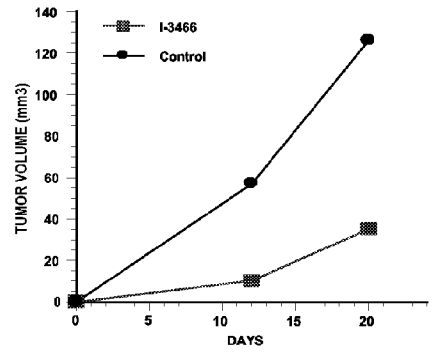
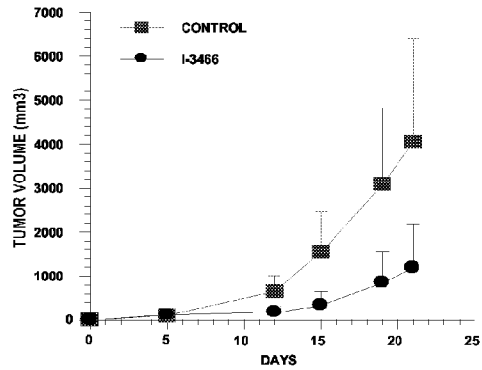
FIGURE 6A　　　　　　　　　　FIGURE 6B
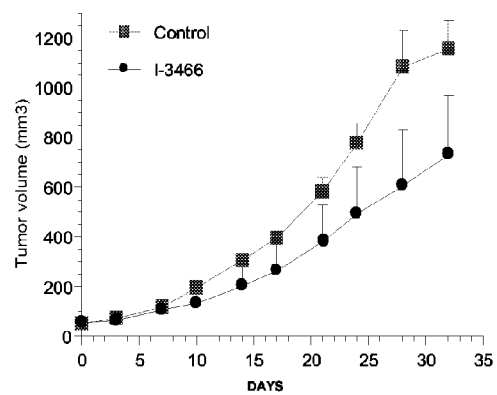
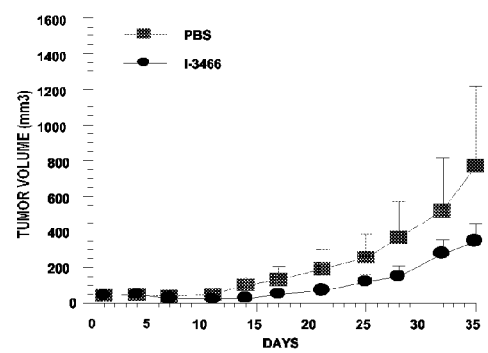
FIGURE 6C　　　　　　　　　　FIGURE 6D
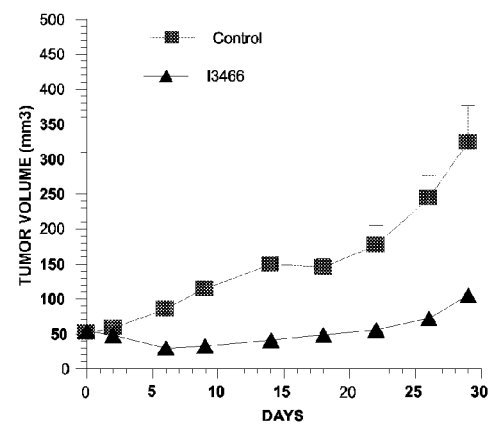
FIGURE 6E

```
                        1*                        *  *          *#  # #       #
   mouse I-3466 LCVR    DIVMSQSPSS LAVSAGEKVT MNCKSSQSLL DSRTRKNYLA WYQQKPGQSP
              P06313    DIVMTQSPDS LAVSLGERAT INCKSSQSVL YSSNNKNYLA WYQQKPGQPP
      VKII 3-1-(1) O11  DIVMTQTPLS LPVTPGEPAS ISCRSSQSLL DSDDGNTYLD WYLQKPGQSP
Humanized I-3466 LCVR   DIVMTQSPDS LAVSLGERAT INCKSSQSLL DSRTRKNYLA WYQQKPGQPP

#  *  **               *          *                # #*#
   mouse I-3466 LCVR    KLLIYWASTR ESGVPDRFTG SGSGTDFTLT ISSVQAEDLA VYYCKQSYNL
              P06313    KLLIYWASTR ESGVPDRFSG SGSGTDFTLT ISSLQAEDVA VYYCQQYDTI
      VKII 3-1-(1) O11  QLLIYTLSYR ASGVPDRFSG SGSGTDFTLK ISRVEAEDVG VYYCNQRIEF
Humanized I-3466 LCVR   KLLIYWASTR ESGVPDRFSG SGSGTDFTLT ISSLQAEDVA VYYCKQSYNL

*##         113
   mouse I-3466 LCVR    FTFGGGTKLE IK-
              P06313    PTFGGGTKVE IKR
      VKII 3-1-(1) O11  P
Humanized I-3466 LCVR   FTFGGGTKVE IKR
```

FIGURE 7

```
                        1                    * ** *     *#  # #      # # 50
   mouse I-3466 HCVR    EVMLVESGGD LVKPGGSLKL SCAASGFTFN NYIMSWVRQT PEKRLEWVAT
            BAC02119    EVQLVESGGD LVQPGGSLRL SCAASGFTFT NYAMSWVRQA PGKGLEWVSA
         VH3 1-3 3-30   QVQLVESGGG VVQPGRSLRL SCAASGFTFS SYGMHWVRQA PGKGLEWVAV
Humanized I-3466 HCVR   EVQLVESGGD LVQPGGSLRL SCAASGFTFN NYIMSWVRQA PGKGLEWVAT 51  *                     *                   # #*#
   mouse I-3466 HCVR    ISGGGSYTFY PDSVKGRFSI SRDNAKNTLY LQMSSLRSED TAMYFCTRNQ
            BAC02119    ISGSGGSTFY ADSVKGRFTI SRDNSKNTLY LQMNSLRAED TAVYYCAKDP
         VH3 1-3 3-30   ISYDGSNKYY ADSVKGRFTI SRDNSKNTLY LQMNSLRAED TAVYYCAK
Humanized I-3466 HCVR   ISGGGSYTFY PDSVKGRFTI SRDNSKNTLY LQMNSLRAED TAVYFCTRNQ 101                       129
   mouse I-3466 HCVR    LLTGMINPLT TPRAWFTYWG QGTLVTVSA
            BAC02119    RIRLWLG--- -DPYYFDYWG QGTLVTVSS
Humanized I-3466 HCVR   LLTGMINPLT TPRAWFTYWG QGTLVTVSS
```

FIGURE 8

ANTI-IGF-IR ANTIBODIES AND USES THEREOF

CROSS REFERENCE TO RELATED APPLICATION

This application is a Divisional of U.S. application Ser. No. 11/989,204, filed on Jan. 22, 2008 and issued as U.S. Pat. No. 8,361,461 on Jan. 29, 2013, which is a 371 National Stage of PCT International Application No. PCT/EP2006/064543, filed on Jul. 21, 2006, and which claims priority to French application 0507829 filed on Jul. 22, 2005, and also claims priority to U.S. Provisional Application No. 60/701,622, filed on Jul. 22, 2005, all of which are hereby expressly incorporated herein by reference into the present application.

The present invention relates to novel antibodies capable of binding specifically to the human insulin-like growth factor I receptor (IGF-IR) and/or capable of specifically inhibiting the tyrosine kinase activity of said IGF-IR, especially monoclonal antibodies of murine, chimeric and humanized origin, as well as the amino acid and nucleic acid sequences coding for these antibodies. In a particular aspect, the invention relates to novel antibodies capable to efficiently inhibiting not only the binding of the ligand IGF1 to IGF-IR but also to efficiently inhibiting the binding of the other ligand, i.e. IGF2, to the same receptor. The invention likewise comprises the use of these antibodies as a medicament for the prophylactic and/or therapeutic treatment of cancers overexpressing IGF-IR, stimulated either by IGF1 and/or IGF2, or any pathology connected with the overexpression of said receptor as well as in processes or kits for diagnosis of illnesses connected with the overexpression of the IGF-IR and/or the IGF-I/Insulin hybrid receptor. The invention finally comprises products and/or compositions comprising such antibodies in combination with, for example, anti-EGFR antibodies and/or compounds and/or anti-cancer agents or agents conjugated with toxins and their use for the prevention and/or the treatment of certain cancers.

The insulin-like growth factor I receptor called IGF-IR is a receptor with tyrosine kinase activity having 70% homology with the insulin receptor IR. IGF-IR is a glycoprotein of molecular weight approximately 350,000. It is a hetero-tetrameric receptor of which each half—linked by disulfide bridges—is composed of an extracellular α-subunit and of a transmembrane β-subunit. IGF-IR binds IGF1 and IGF2 with a very high affinity (Kd #1 nM) but is equally capable of binding to insulin with an affinity 100 to 1000 times less. Conversely, the IR binds insulin with a very high affinity although the IGFs only bind to the insulin receptor with a 100 times lower affinity. The tyrosine kinase domain of IGF-IR and of IR has a very high sequence homology although the zones of weaker homology respectively concern the cysteine-rich region situated on the α-subunit and the C-terminal part of the β-subunit. The sequence differences observed in the α-subunit are situated in the binding zone of the ligands and are therefore at the origin of the relative affinities of IGF-IR and of IR for the IGFs and insulin respectively. The differences in the C-terminal part of the β-subunit result in a divergence in the signalling pathways of the two receptors; IGF-IR mediating mitogenic, differentiation and antiapoptosis effects, while the activation of the IR principally involves effects at the level of the metabolic pathways (Baserga et al., Biochim. Biophys. Acta, 1332:F105-126, 1997; Baserga R., Exp. Cell. Res., 253:1-6, 1999).

The cytoplasmic tyrosine kinase proteins are activated by the binding of the ligand to the extracellular domain of the receptor. The activation of the kinases in its turn involves the stimulation of different intra-cellular substrates, including IRS-1, IRS-2, Shc and Grb 10 (Peruzzi F. et al., J. Cancer Res. Clin. Oncol., 125:166-173, 1999). The two major substrates of IGF-IR are IRS and Shc which mediate, by the activation of numerous effectors downstream, the majority of the growth and differentiation effects connected with the attachment of the IGFs to this receptor. The availability of substrates can consequently dictate the final biological effect connected with the activation of the IGF-IR. When IRS-1 predominates, the cells tend to proliferate and to transform. When Shc dominates, the cells tend to differentiate (Valentinis B. et al., J. Biol. Chem. 274:12423-12430, 1999). It seems that the route principally involved for the effects of protection against apoptosis is the phosphatidyl-inositol 3-kinases (PI 3-kinases) route (Prisco M. et al., Horm. Metab. Res., 31:80-89, 1999; Peruzzi F. et al., J. Cancer Res. Clin. Oncol., 125:166-173, 1999).

The role of the IGF system in carcinogenesis has become the subject of intensive research in the last ten years. This interest followed the discovery of the fact that in addition to its mitogenic and antiapoptosis properties, IGF-IR seems to be required for the establishment and the maintenance of a transformed phenotype. In fact, it has been well established that an overexpression or a constitutive activation of IGF-IR leads, in a great variety of cells, to a growth of the cells independent of the support in media devoid of fetal calf serum, and to the formation of tumors in nude mice. This in itself is not a unique property since a great variety of products of overexpressed genes can transform cells, including a good number of receptors of growth factors. However, the crucial discovery which has clearly demonstrated the major role played by IGF-IR in the transformation has been the demonstration that the R-cells, in which the gene coding for IGF-IR has been inactivated, are totally refractory to transformation by different agents which are usually capable of transforming the cells, such as the E5 protein of bovine papilloma virus, an overexpression of EGFR or of PDGFR, the T antigen of SV 40, activated ras or the combination of these two last factors (Sell C. et al., Proc. Natl. Acad. Sci., USA, 90:11217-11221, 1993; Sell C. et al., Mol. Cell. Biol., 14:3604-3612, 1994; Morrione A. J., Virol., 69:5300-5303, 1995; Coppola D. et al., Mol. Cell. Biol., 14:4588-4595, 1994; DeAngelis T et al., J. Cell. Physiol., 164:214-221, 1995).

IGF-IR is expressed in a great variety of tumors and of tumor lines and the IGFs amplify the tumor growth via their attachment to IGF-IR. Other arguments in favor of the role of IGF-IR in carcinogenesis come from studies using murine monoclonal antibodies directed against the receptor or using negative dominants of IGF-IR. Actually, murine monoclonal antibodies directed against IGF-IR inhibit the proliferation of numerous cell lines in culture and the growth of tumor cells in vivo (Arteaga C. et al., Cancer Res., 49:6237-6241, 1989; Li et al., Biochem. Biophys. Res. Com., 196:92-98, 1993; Zia F. et al., J. Cell. Biol., 24:269-275, 1996; Scotlandi K. et al., Cancer Res., 58:4127-4131, 1998). It has likewise been shown in the works of Jiang et al. (Oncogene, 18:6071-6077, 1999) that a negative dominant of IGF-IR is capable of inhibiting tumor proliferation.

Such antibodies capable to bind specificaly to the IGF-IR have been described and several patent applications have been filed. As an example, we can mentioned the patent application WO 03/059951, filed by the Applicant, wherein a monoclonal antibody able to bind to IGF-IR, called 7C10, is described. Others patent applications can be mentioned as WO 02/053596 (PFIZER INC. and ABGENIX INC.), WO 03/100008 (SCHERING CORPORATION) or WO 03/106621 (IMMUNOGEN INC.). All these applications are claiming antibodies capable to specifically bind to the IGF-IR and/or to inhibit its activity.

Although it is considered as an evident property for each of these antibodies, nothing in the specification of these applications clearly demonstrate that these antibodies are capable to inhibit efficiently the binding of both natural ligands to IGF-IR and, more particularly the binding IGF2 to IGF-IR. In vitro data such as inhibition of proliferation IGF1 and IGF2 induced were shown in these applications and demonstrated that the described antibodies are able to inhibit efficiently both IGF1 and IGF2-induced proliferation. However, as the major part of described antibodies displayed the capacity of inducing a partial down-regulation of IGF-IR, it is not evident that the antiproliferative properties are directly linked to a displacement of both IGF1 and IGF2 from IGF-IR.

Actually, for example, data shown in WO 03/106621 are only dealing with IGF1 and under no circumstances with an eventual inhibition of the binding of the IGF2 to IGF-IR (see Example C, pages 33-35 and FIG. 3, and Example D, pages 35-37 and FIGS. 4-6).

The same observations can be made for WO 02/053596 (see Example IV, page 78-79 and FIG. 3, and Example VII, page 82 and FIG. 4).

Amongst all the presently identified patent applications describing the discovery of monoclonal or recombinant antibodies directed against the human IGF-IR (hIGF-IR), only two of them (WO 2004/087756 and WO 2005/005635) are really showing an efficacy of the antibodies, respectively AK1a and AK18, to inhibit [$^{125}$I]IGF2 binding to hIGF-IR.

The experimental procedure, identical in both cases, is based on competition binding on human colorectal adenocarcinoma (HT29) intact cells. Although the described procedure is sound, no positive controls such as competition by natural hIGF-IR ligands (IGF1 and IGF2) is presented, making the data on competition binding suspicious. On the other hand, only incomplete competition was shown (maximally 80% inhibition of [$^{125}$I]IGF2 binding for both AK1a and AK18 antibody), even at high antibody concentration, making the development of more efficacious antibodies necessary for enhanced therapeutic efficacy in humans. A last controversial point concerning the putative inhibition of IGF2-mediated responses by AK1a and AK18 is the absence of examples showing an inhibition of functional IGF2-stimulated signaling mediated by hIGF-IR. Indeed, even if competition of IGF2 binding is happening, it must be associated with a concomitant inhibition of downstream hIGF-IR signalling and such evidence must be exemplified to provide mechanistic evidence for antibody functional efficacy.

The object of the present invention is to be able to have available a murine monoclonal antibody, preferably a chimerized or humanized antibody, which will recognize IGF-IR specifically with great affinity and which is also able to inhibit not only the binding of IGF1 to IGF-IR but also the binding of IGF2 to IGF-IR. This antibody will interact little or not at all with the IR. Its attachment will be able to inhibit the in vitro growth of cell lines overexpressing IGF-IR by interacting principally with the signal transduction pathways activated during IGF1/IGF-IR and IGF2/IGF-IR interactions. This antibody will be able to be active in vivo on all tumors types expressing IGF-IR including estrogen-dependent breast tumors and prostate tumors, which is not the case for the anti-IGF-IR monoclonal antibodies (written MAb or MAB) currently available. In effect, αIR3, which refers to the domain of IGF-IR, totally inhibits the growth of estrogen-dependent tumors of the breast (MCF-7) in vitro but is without effect on the corresponding model in vivo (Arteaga C. et al., J. Clin. Invest. 84:1418-1423, 1989). In the same way, the scFv-Fc fragment derived from the murine monoclonal 1117 is only weakly active on the tumor of the breast MCF-7 and totally inactive on an androgen-independent tumor of the prostate (Li S. L. et al., Cancer Immunol. Immunother., 49:243-252, 2000).

In a surprising manner, the inventors have generated a murine monoclonal antibody described as I-3466, recognising IGF-IR and corresponding to all of the criteria stated above, that is to say to a nonrecognition of the receptor on the insulin, to an in vitro blockage of the IGF1 and particularly the IGF2 proliferation induced but likewise to the in vivo inhibition of the growth of different tumors expressing IGF-IR among which are an osteosarcoma and prostate tumors. Furthermore, it has been shown that these antibodies inhibit the IGF1- and/or IGF2-induced phosphorylation of the tyrosine of the beta chain of IGF-IR both on both MCF-7 and HT29 cells. Moreover, it has likewise been established that these antibodies cause the internalization of said receptor and its degradation contrary to what is usually observed with natural ligands which allow the rapid recycling of the receptor on the surface of the cells. It has been possible to characterize these antibodies by their peptidic and nucleic sequence, especially by the sequence of their regions determining their complementarity (CDR) for IGF-IR.

Thus, according to a first embodiment, a subject of the present invention is an isolated antibody, or one of its functional fragments, said antibody or one of its said fragments being capable of binding specifically to the human insulin-like growth factor I receptor and/or capable of specifically inhibiting the tyrosine kinase activity of said IGF-IR receptor, characterized in that it is capable of inhibiting the natural attachment of its first ligand IGF1 with an $IC_{50}$ of less than 0.3 nM, preferentially less than 0.03 nM and also capable of inhibiting the natural attachment of its second ligand IGF2 with an $IC_{50}$ of less than 0.3 nM, preferentially less than 0.1 nM.

More particularly, the invention concerns an isolated antibody, or a functional immunogenic fragment thereof, having a binding affinity for the human insulin-like growth factor I receptor (IGF-IR), characterized in that upon binding said IGF-IR, it inhibits the binding of the native binding partner IGF1 to said IGF-IR with an $IC_{50}$ of less than 0.3 nM, preferentially less than 0.03 nM and it also inhibits the binding of the native binding partner IGF2 to said IGF-IR with an $IC_{50}$ of less than 0.3 nM, preferentially less than 0.1 nM.

In addition, the invention concerns an isolated antibody, or a functional immunogenic fragment thereof, having a tyrosine kinase of the human insulin-like growth factor I receptor (IGF-IR) inhibiting activity, characterized in that upon binding said IGF-IR, it inhibits the binding of the native binding partner IGF1 to said IGF-IR with an $IC_{50}$ of less than 0.3 nM, preferentially less than 0.03 nM and it also inhibits the binding of the native binding partner IGF2 to said IGF-IR with an $IC_{50}$ of less than 0.3 nM, preferentially less than 0.1 nM.

In the present application, $IC_{50}$ have been determined graphically as explained in example 2.

Regarding the state on the art, Roche antibody referenced 18 (WO 2004/087756 and WO 2005/005635) have an average $IC_{50}$ for both for IGF1 and IGF2 which is about 0.3 nM (see example 6 of WO 2005/005635), i.e. more than the $IC_{50}$ obtained for the antibody I-3466 (see example 2).

In the present description, the terms "to bind" and "to attach" have the same meaning and are inter-changeable.

According to another embodiment of the invention, the antibody is also capable to bind the IGF-I/Insulin hybrid receptor.

Actually, IGF-IR shows a high homology with the Insulin receptor (IR) which exists under two isoforms A and B.

Sequences of IR, isoforms A and B, are registered under Accession Numbers X02160 and M10051, respectively, in the NCBI Genbank. Other datas, without limitations, relating to IR are incorporated herein by references (Vinten et al., 1991, Proc. Natl. Acad. Sci. USA, 88:249-252; Belfiore et al., 2002, The Journal of Biological Chemistry, 277:39684-39695; Dumesic et al., 2004, The Journal of Endocrinology & Metabolism, 89(7):3561-3566).

The IGF-IR and IR are tetrameric glycoproteins composed of two extracellular α- and two transmembrane β-subunits linked by disulfide bonds. Each α-subunit, containing the ligand-binding site is approximately 130- to 135-kDa, whereas each β-subunit containing the tyrosine kinase domain is approximately 90- to 95-kDa. These receptors share more than 50% overall amino acid sequence similarity and 84% similarity in the tyrosine kinase domain. After ligand binding, phosphorylated receptors recruit and phosphorylate docking proteins, including the insulin receptor substrate-1 protein family (IRS1), Gab1 and Shc (Avruch, 1998, Mol. Cell. Biochem., 182, 31-48; Roth et al., 1988, Cold Spring Harbor Symp. Quant. Biol., 53, 537-543; White, 1998, Mol. Cell. Biochem. 182, 3-11; Laviola et al., 1997, J. Clin. Invest., 99, 830-837; Cheatham et al., 1995, Endocr. Rev., 16, 117-142), leading to the activation of different intracellular mediators. Although both the IR and IGF-IR similarly activate major signalling pathways, differences exist in the recruitment of certain docking proteins and intracellular mediators between both receptors (Sasaoka et al., 1996, Endocrinology 137, 4427-4434; Nakae et al., 2001, Endocr. Rev., 22, 818-835; Dupont and Le Roith, 2001, Horm. Res. 55, Suppl. 2, 22-26; Koval et al., 1998, Biochem. J., 330, 923-932). These differences are the basis for the predominant metabolic effects elicited by IR activation and the predominant mitogenic, transforming and anti-apoptotic effects elicited by IGF-IR activation (De Meyts et al., 1995, Ann. N.Y. Acad. Sci., 766, 388-401; Singh et al., 2000; Prisco et al., 1999, Horm. Metab. Res., 31, 80-89; Kido et al., 2001, J. Clin. Endocrinol. Metab., 86, 972-979). Insulin binds with high affinity to the IR (100-fold higher than to the IGF-IR), whereas insulin-like growth factors (IGF1 and IGF2) bind to the IGF-IR with 100-fold higher affinity than to the IR.

The human IR exists in two isoforms, IR-A and IR-B, generated by alternative splicing of the IR gene that either excludes or includes 12 amino acid residues encoded by a small exon (exon 11) at the carboxy-terminus of the IR α-subunit. The relative abundance of IR isoforms is regulated by tissue specific and unknown factors (Moller et al., 1989, Mol. Endocrinol., 3, 1263-1269; Mosthaf et al., 1990, EMBO J., 9, 2409-2413). IR-B is the predominant IR isoform in normal adult tissues (adipose tissue, liver and muscle) that are major target tissues for the metabolic effects of insulin (Moller et al., 1989; Mosthaf et al., 1990). IR-A is the predominant isoform in fetal tissues and mediates fetal growth in response to IGF2 (Frasca et al., 1999, Mol. Cell. Biol., 19, 3278-3288), as also suggested by genetic studies carried out in transgenic mice (DeChiara et al., 1990, Nature 345, 78-80; Louvi et al., 1997, Dev. Biol. 189, 33-48). Moreover, when cells transform and become malignant, dedifferentiation is often associated with an increased IR-A relative abundance (Pandini et al., 2002, The Journal of Biological Chemistry, Vol. 277, N° 42, pp 39684-39695).

Given the high degree of homology, the insulin and IGF-I half-receptors (composed of one α- and one β-subunit) can heterodimerize, leading to the formation of insulin/IGF-I hybrid receptors (Hybrid-R) (Soos et al., 1990, Biochem J., 270, 383-390; Kasuya et al., 1993, Biochemistry 32, 13531-13536; Seely et al., 1995, Endocrinology 136, 1635-1641; Bailyes et al., 1997, Biochem J., 327, 209-215).

Both IR isoforms are equally able to form hybrids with IGF-IR. Hybrid-R, however, have different functional characteristics. Hybrid-RsB has reduced affinity for IGF1 and especially for IGF2. In contrast, Hybrid-RsA has a high affinity for IGF1 and bind also IGF2 and insulin at a physiological concentration range. The expression of Hybrid-RsA up-regulates the IGF system by two different mechanisms i) binding (with high affinity) and activation by both IGF1 and IGF2 (which do not occur with the Hybrid-RsB), ii) activation of the IGF-IR pathway after insulin binding. Insulin binding to Hybrid-RsA phosphorylates the IGF-IR β-subunit and activates an IGF-IR-specific substrate (CrkII) so that Hybrid-RsA shifts insulin to IGF-IR signaling (Pandini et al., 2002).

In several tissues, like liver, spleen or placenta, Hybrid-R are more represented than IGF-IR (Bailyes et al., 1997). As tumor tissues overexpress, or present an abnormal activation, both IGF-IR and IR-A (Frasca et al., 1999; Sciacca et al., 1999, Oncogene 18, 2471-2479; Vella et al., 2001, Mol. Pathol., 54, 121-124), Hybrid-RsA may also be overexpressed in a variety of human malignancies, including thyroid and breast cancers providing a selective growth advantage to malignant cells able to respond by a type IGF-IR signalisation following a stimulation by IGF1 and/or IGF2 but also by insulin at physiological concentrations (Bailyes et al., 1997; Pandini et al., 1999, Clin. Cancer Res. 5, 1935-1944; Belfiore et al., 1999, Biochimie (Paris) 81, 403-407; Frasca et al., 1999; Sciacca et al., 1999; Vella et al., 2001).

According to the invention, antibodies are also characterized in that they are capable of binding to the Hybrid-R and, if necessary, preferably moreover capable of inhibiting the natural attachment of the ligands insulin, IGF 1 and/or IGF-2 of Hybrid-R and/or capable of specifically inhibiting the tyrosine kinase activity of said Hybrid-R.

An object of the invention is an antibody, or one of its functional fragments, characterized in that it is also capable of inhibiting 100% of the IGF1 and/or IGF2 induced phosphorylation of the IGF-IR beta-chain (preferentially on HT29 cells).

In another aspect, the antibody, or one of its functional fragments, according to the invention is characterized in that it does not present any agonistic intrinsic activity.

The antibody, or one of its functional fragments, according to the invention, is moreover characterized in that it is capable of inducing, using the same FACS analysis method:
i) at least 30% of the IGF-IR internalization on HT29 cells, and/or
ii) at least 85% of the IGF-IR internalization on MCF-7 cells.

A characteristic of the antibody, or one of its functional fragments, according to the invention, is its capacity of inducing, using the same FACS analysis method:
i) at least 50% of the IGF-IR degradation on HT29 cells, and/or
ii) at least 65% of the IGF-IR degradation on MCF-7 cells.

In another embodiment, the antibody, or one of its functional fragments, according to the invention, is characterized in that it is able to inhibit both IGF1 and IGF2-induced in vitro proliferation of MCF-7 cells with $IC_{50s}$ at least equal to 1 nM and preferentially at least 0.7 and 0.5 nM respectively for IGF1 and IGF2 experiments.

The antibody, or one of its functional fragments, according to the invention is also characterized in that it is able to inhibit the in vivo growth of tumor cell lines.

The antibodies according to the present invention are preferably specific monoclonal antibodies, especially of murine, chimeric or humanized origin, which can be obtained according to the standard methods well known to the person skilled in the art.

In general, for the preparation of monoclonal antibodies or their functional fragments, especially of murine origin, it is possible to refer to techniques which are described in particular in the manual "Antibodies" (Harlow and Lane, Antibodies: A Laboratory Manual, Cold Spring Harbor Laboratory, Cold Spring Harbor N.Y., pp. 726, 1988) or to the technique of preparation from hybridomas described by Kohler and Milstein (Nature, 256:495-497, 1975).

The monoclonal antibodies according to the invention can be obtained, for example, from an animal cell immunized against the IGF-IR, or one of its fragments containing the epitope specifically recognized by said monoclonal antibodies according to the invention. Said IGF-IR, or one of its said fragments, can especially be produced according to the usual working methods, by genetic recombination starting with a nucleic acid sequence contained in the cDNA sequence coding for the IGF-IR or by peptide synthesis starting from a sequence of amino acids comprised in the peptide sequence of the IGF-IR.

The monoclonal antibodies according to the invention can, for example, be purified on an affinity column on which the IGF-IR or one of its fragments containing the epitope specifically recognized by said monoclonal antibodies according to the invention has previously been immobilized. More particularly, said monoclonal antibodies can be purified by chromatography on protein A and/or G, followed or not followed by ion-exchange chromatography aimed at eliminating the residual protein contaminants as well as the DNA and the LPS, in itself followed or not followed by exclusion chromatography on Sepharose gel in order to eliminate the potential aggregates due to the presence of dimers or of other multimers. In an even more preferred manner, the whole of these techniques can be used simultaneously or successively.

Chimeric or humanized antibodies are likewise included in antibodies according to the present invention.

By chimeric antibody, it is intended to indicate an antibody which contains a natural variable (light chain and heavy chain) region derived from an antibody of a given species in combination with the light chain and heavy chain constant regions of an antibody of a species heterologous to said given species.

The antibodies or their fragments of chimeric type according to the invention can be prepared by using the techniques of genetic recombination. For example, the chimeric antibody can be produced by cloning a recombinant DNA containing a promoter and a sequence coding for the variable region of a nonhuman, especially murine, monoclonal antibody according to the invention and a sequence coding for the constant region of human antibody. A chimeric antibody of the invention encoded by such a recombinant gene will be, for example, a mouse-man chimera, the specificity of this antibody being determined by the variable region derived from the murine DNA and its isotype determined by the constant region derived from the human DNA. For the methods of preparation of chimeric antibodies, it is possible, for example, to refer to the document Verhoeyn et al. (BioEssays, 8:74, 1988).

By humanized antibody, it is intended to indicate an antibody which contains CDR regions derived from an antibody of nonhuman origin, the other parts of the antibody molecule being derived from one (or from several) human antibodies. Moreover, some of the residues of the segments of the skeleton (called FR) can be modified in order to conserve the affinity of the binding (Jones et al., Nature, 321:522-525, 1986; Verhoeyen et al., Science, 239:1534-1536, 1988; Riechmann et al., Nature, 332:323-327, 1988).

The humanized antibodies according to the invention or their fragments can be prepared by techniques known to the person skilled in the art (such as, for example, those described in the documents Singer et al., J. Immun., 150:2844-2857, 1992; Mountain et al., Biotechnol. Genet. Eng. Rev., 10:1-142, 1992; or Bebbington et al., Bio/Technology, 10:169-175, 1992). Such humanized antibodies according to the invention are preferred for their use in in vitro diagnostic methods, or in vivo prophylactic and/or therapeutic treatment. Other humanization method are known by the man skill in the art as, for example, the "CDR Grafting" method described by Protein Design Lab (PDL) in the patent applications EP 0 451 261, EP 0 682 040, EP 0 9 127, EP 0 566 647 or U.S. Pat. No. 5,530,101, U.S. Pat. No. 6,180,370, U.S. Pat. No. 5,585,089 and U.S. Pat. No. 5,693,761. The following patent applications can also be mentioned: U.S. Pat. No. 5,639,641; U.S. Pat. No. 6,054,297; U.S. Pat. No. 5,886,152 and U.S. Pat. No. 5,877,293. By functional fragment of an antibody according to the invention, it is intended to indicate in particular an antibody fragment, such as Fv, scFv (sc for single chain), Fab, $F(ab')_2$, Fab', scFv-Fc fragments or diabodies, or any fragment of which the half-life time would have been increased by chemical modification, such as the addition of poly(alkylene) glycol such as poly(ethylene)glycol ("PEGylation") (pegylated fragments called Fv-PEG, scFv-PEG, Fab-PEG, $F(ab')_2$-PEG or Fab'-PEG) ("PEG" for Poly(Ethylene)Glycol), or by incorporation in a liposome, said fragments having at least one of the characteristic CDRs of sequence SEQ ID No. 1, 2, 3, 4, 5 or 6 according to the invention, and, especially, in that it is capable of exerting in a general manner an even partial activity of the antibody from which it is descended, such as in particular the capacity to recognize and to bind to the IGF-IR, and, if necessary, to inhibit the activity of the IGF-IR.

Preferably, said functional fragments will be constituted or will comprise a partial sequence of the heavy or light variable chain of the antibody from which they are derived, said partial sequence being sufficient to retain the same specificity of binding as the antibody from which it is descended and a sufficient affinity, preferably at least equal to $1/100$, in a more preferred manner to at least $1/10$, of that of the antibody from which it is descended, with respect to the IGF-IR.

Such a functional fragment will contain at the minimum 5 amino acids, preferably 10, 15, 25, 50 and 100 consecutive amino acids of the sequence of the antibody from which it is descended.

Preferably, these functional fragments will be fragments of Fv, scFv, Fab, $F(ab')_2$, F(ab'), scFv-Fc type or diabodies, which generally have the same specificity of binding as the antibody from which they are descended. According to the present invention, antibody fragments of the invention can be obtained starting from antibodies such as described above by methods such as digestion by enzymes, such as pepsin or papain and/or by cleavage of the disulfide bridges by chemical reduction. In another manner, the antibody fragments comprised in the present invention can be obtained by techniques of genetic recombination likewise well known to the person skilled in the art or else by peptide synthesis by means of, for example, automatic peptide synthesizers such as those supplied by the company Applied Biosystems, etc.

In a more preferred manner, the invention comprises the antibodies, or their functional fragments, according to the present invention, especially chimeric or humanized antibodies, obtained by genetic recombination or by chemical synthesis.

More particularly, according to a preferred embodiment of the invention, the antibody is characterized in that it comprises a light chain comprising at least one complementarity determining region CDR chosen from the CDRs of sequence SEQ ID No. 1, 3 or 5, or at least one CDR whose sequence has at least 80% identity after optimum alignment with the sequence SEQ ID No. 1, 3 or 5, or in that it comprises a heavy chain comprising at least one CDR chosen from the CDRs of sequence SEQ ID No. 2, 4 or 6, or at least one CDR whose sequence has at least 80% identity after optimum alignment with the sequence SEQ ID No. 2, 4 or 6.

In the present description, the terms polypeptides, polypeptide sequences, peptides and proteins attached to antibody compounds or to their sequence are interchangeable.

It must be understood here that the invention does not relate to the antibodies in natural form, that is to say they are not in their natural environment but that they have been able to be isolated or obtained by purification from natural sources, or else obtained by genetic recombination, or by chemical synthesis, and that they can then contain unnatural amino acids as will be described further on.

By CDR region or CDR, it is intended to indicate the hypervariable regions of the heavy and light chains of the immunoglobulins as defined by Kabat et al. (Kabat et al., Sequences of proteins of immunological interest, 5th Ed., U.S. Department of Health and Human Services, NIH, 1991, and later editions). 3 heavy chain CDRs and 3 light chain CDRs exist. The term CDR or CDRs is used here in order to indicate, according to the case, one of these regions or several, or even the whole, of these regions which contain the majority of the amino acid residues responsible for the binding by affinity of the antibody for the antigen or the epitope which it recognizes.

By "percentage of identity" between two nucleic acid or amino acid sequences in the sense of the present invention, it is intended to indicate a percentage of nucleotides or of identical amino acid residues between the two sequences to be compared, obtained after the best alignment (optimum alignment), this percentage being purely statistical and the differences between the two sequences being distributed randomly and over their entire length. The comparisons of sequences between two nucleic acid or amino acid sequences are traditionally carried out by comparing these sequences after having aligned them in an optimum manner, said comparison being able to be carried out by segment or by "comparison window". The optimum alignment of the sequences for the comparison can be carried out, in addition to manually, by means of the local homology algorithm of Smith and Waterman (1981) [Ad. App. Math. 2:482], by means of the local homology algorithm of Neddleman and Wunsch (1970) [J. Mol. Biol. 48: 443], by means of the similarity search method of Pearson and Lipman (1988) [Proc. Natl. Acad. Sci. USA 85:2444), by means of computer software using these algorithms (GAP, BESTFIT, FASTA and TFASTA in the Wisconsin Genetics Software Package, Genetics Computer Group, 575 Science Dr., Madison, Wis., or else by BLAST N or BLAST P comparison software).

The percentage of identity between two nucleic acid or amino acid sequences is determined by comparing these two sequences aligned in an optimum manner and in which the nucleic acid or amino acid sequence to be compared can comprise additions or deletions with respect to the reference sequence for an optimum alignment between these two sequences. The percentage of identity is calculated by determining the number of identical positions for which the nucleotide or the amino acid residue is identical between the two sequences, by dividing this number of identical positions by the total number of positions in the comparison window and by multiplying the result obtained by 100 in order to obtain the percentage of identity between these two sequences.

For example, it is possible to use the BLAST program, "BLAST 2 sequences" (Tatusova et al., "Blast 2 sequences—a new tool for comparing protein and nucleotide sequences", FEMS Microbiol Lett. 174:247-250) available on the site http://www.ncbi.nlm.nih.gov/gorf/b12.html, the parameters used being those given by default (in particular for the parameters "open gap penalty": 5, and "extension gap penalty": 2; the matrix chosen being, for example, the matrix "BLOSUM 62" proposed by the program), the percentage of identity between the two sequences to be compared being calculated directly by the program.

By amino acid sequence having at least 80%, preferably 85%, 90%, 95% and 98% identity with a reference amino acid sequence, those having, with respect to the reference sequence, certain modifications, in particular a deletion, addition or substitution of at least one amino acid, a truncation or an elongation are preferred. In the case of a substitution of one or more consecutive or nonconsecutive amino acid(s), the substitutions are preferred in which the substituted amino acids are replaced by "equivalent" amino acids. The expression "equivalent amino acids" is aimed here at indicating any amino acid capable of being substituted with one of the amino acids of the base structure without, however, essentially modifying the biological activities of the corresponding antibodies and such as will be defined later, especially in the examples.

Alternative embodiments of the invention propose anti-IGF-IR antibodies having other amino acid sequence modification(s) contained therein. For example, it may be desirable to improve the binding affinity and/or other biological properties of the antibody. Amino acid sequence variants of the anti-IGF-IR antibody are prepared by introducing appropriate nucleotide changes into the anti-IGF-IR antibody nucleic acid, or by peptide synthesis. Such modifications include, for example, deletions from, and/or insertions into and/or substitutions of, residues within the amino acid sequences of the anti-IGF-IR antibody. Any combination of deletion, insertion, and substitution is made to arrive at the final construct, provided that the final construct possesses the desired characteristics. The amino acid changes also may alter post-translational processes of the anti-IGF-IR antibody, such as changing the number or position of glycosylation sites.

A useful method for identification of certain residues or regions of the anti-IGF-IR antibody that are preferred locations for mutagenesis is called "alanine scanning mutagenesis" as described by Cunningham and Wells in Science, 244:1081-1085 (1989). Here, a residue or group of target residues are identified (e.g., charged residues such as arg, asp, his, lys, and glu) and replaced by a neutral or negatively charged amino acid (most preferably alanine or polyalanine) to affect the interaction of the amino acids with IGF-IR antigen. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, ala scanning or random mutagenesis is conducted at the target codon or region and the expressed anti-IGF-IR antibody variants are screened for the desired activity.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an anti-IGF-IR antibody. with an N-terminal methionyl residue or the antibody fused to a cytotoxic polypeptide. Other insertional variants of the anti-IGF-IR antibody molecule include the fusion to the N- or C-terminus of the anti-IGF-IR antibody to an enzyme (e.g. for ADEPT) or a polypeptide which increases the serum half-life of the antibody.

Another type of variant is an amino acid substitution variant. These variants have at least one amino acid residue in the anti-IGF-IR antibody molecule replaced by a different residue. The sites of greatest interest for substitutional mutagenesis include the hypervariable regions, but FR alterations are also contemplated. Conservative substitutions are shown in Table 1 under the heading of "preferred substitutions". If such substitutions result in a change in biological activity, then more substantial changes, denominated "exemplary substitutions" in Table 1, or as further described below in reference to amino acid classes, may be introduced and the products screened.

TABLE 1

Amino Acid Substitutions

| Original Residue | Exemplary Substitutions | Preferred Substitutions |
|---|---|---|
| Ala (A) | val; leu; ile | val |
| Arg (R) | lys; gln; asn | lys |
| Asn (N) | gln; his; asp; lys; arg | gln |
| Asp (D) | glu; asn | glu |
| Cys (C) | ser; ala | ser |
| Gln (Q) | asn; glu | asn |
| Glu (E) | asp; gln | asp |
| Gly (G) | ala | ala |
| His (H) | asn; gln; lys; arg | arg |
| Ile (I) | leu; val; met; ala; phe; norleucine | leu |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala; tyr | tyr |
| Pro (P) | ala | ala |
| Ser (S) | thr | thr |
| Thr (T) | ser | ser |
| Trp (W) | tyr; phe | tyr |
| Tyr (Y) | trp; phe; thr; ser | phe |
| Val (V) | ile; leu; met; phe; ala; norleucine | leu |

Substantial modifications in the biological properties of the antibody can be accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:
(1) hydrophobic: norleucine, met, ala, val, leu, ile;
(2) neutral hydrophilic: cys, ser, thr;
(3) acidic: asp, glu;
(4) basic: asn, gln, his, lys, arg;
(5) residues that influence chain orientation: gly, pro; and
(6) aromatic: trp, tyr, phe.

Non-conservative substitutions will entail exchanging a member of one of these classes for another class.

Any cysteine residue not involved in maintaining the proper conformation of the anti-IGF-IR antibody also may be substituted, generally with serine, to improve the oxidative stability of the molecule and prevent aberrant crosslinking. Conversely, cysteine bond(s) may be added to the antibody to improve its stability (particularly where the antibody is an antibody fragment such as an Fv fragment).

A particularly preferred type of substitutional variant involves substituting one or more hypervariable region residues of a parent antibody (e.g. a humanized or human antibody). Generally, the resulting variant(s) selected for further development will have improved biological properties relative to the parent antibody from which they are generated. A convenient way for generating such substitutional variants involves affinity maturation using phage display. Briefly, several hypervariable region sites (e.g. 6-7 sites) are mutated to generate all possible amino substitutions at each site. The antibody variants thus generated are displayed in a monovalent fashion from filamentous phage particles as fusions to the gene III product of M13 packaged within each particle. The phage-displayed variants are then screened for their biological activity (e.g. binding affinity) as herein disclosed. In order to identify candidate hypervariable region sites for modification, alanine scanning mutagenesis can be performed to identify hypervariable region residues contributing significantly to antigen binding. Alternatively, or additionally, it may be beneficial to analyze a crystal structure of the antigen-antibody complex to identify contact points between the antibody and human IGF-IR. Such contact residues and neighboring residues are candidates for substitution according to the techniques elaborated herein. Once such variants are generated, the panel of variants is subjected to screening as described herein and antibodies with superior properties in one or more relevant assays may be selected for further development.

Another type of amino acid variant of the antibody alters the original glycosylation pattern of the antibody. By altering is meant deleting one or more carbohydrate moieties found in the antibody, and/or adding one or more glycosylation sites that are not present in the antibody.

Glycosylation of antibodies is typically either N-linked or O-linked N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceyl-galactosamine, galactose, or xylose to a hydroxyamino acid, most commonly serine or threonine, although 5-hydroxyproline or 5-hydroxylysine may also be used.

Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

Nucleic acid molecules encoding amino acid sequence variants of the subject anti-IGF-IR antibody are prepared by a variety of methods known in the art. These methods include, but are not limited to, isolation from a natural source (in the case of naturally occurring amino acid sequence variants) or preparation by oligonucleotide-mediated (or site-directed)

mutagenesis, PCR mutagenesis, and cassette mutagenesis of an earlier prepared variant or a non-variant version of the anti-IGF-IR antibody.

At times, it may be desirable to modify the antibody of the invention with respect to effector function, e.g. so as to enhance antigen-dependent cell-mediated cytotoxicity (ADCC) and/or complement dependent cytotoxicity (CDC) of the antibody. This may be achieved by introducing one or more amino acid substitutions in an Fc region of the antibody. Alternatively or additionally, cysteine residue(s) may be introduced in the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al., J. Exp Med., 176:1191-1195 (1992) and Shopes, B. J. Immunol., 148:2918-2922 (1992). Homodimeric antibodies with enhanced anti-tumor activity may also be prepared using heterobifunctional cross-linkers as described in Wolff et al., Cancer Research, 53:2560-2565 (1993). Alternatively, an antibody can be engineered which has dual Fc regions and may thereby have enhanced complement lysis and ADCC capabilities. See Stevenson et al., Anti-Cancer Drug Design 3:219-230 (1989).

Likewise, to increase the serum half life of the antibody, one may incorporate a salvage receptor binding epitope into the antibody (especially an antibody fragment) as described in U.S. Pat. No. 5,739,277, for example. As used herein, the term "salvage receptor binding epitope" refers to an epitope of the Fc region of an IgG molecule (e.g., $IgG_1$, $IgG_2$, $IgG_3$, or $IgG_4$) that is responsible for increasing the in vivo serum half-life of the IgG molecule.

In a more preferred manner, the present invention relates to an antibody or one of its functional fragments, according to the invention, characterized in that it comprises a heavy chain comprising at least two of the three CDRs or the three CDRs of sequence SEQ ID Nos. 2, 4 and 6, or at least two of three CDRs or three CDRs of sequence respectively having at least 80% identity after optimum alignment with the sequence SEQ ID Nos. 2, 4 and 6.

In a more preferred embodiment, a subject of the invention is an antibody or one of its functional fragments according to the invention, characterized in that it comprises a light chain comprising at least two of the three CDRs or the three CDRs of sequence SEQ ID Nos. 1, 3 and 5, or at least two of three CDRs or three CDRs of sequence respectively having at least 80% identity after optimum alignment with the sequence SEQ ID Nos. 1, 3 and 5.

In a more preferred manner, the antibody or one of its functional fragments according to the invention is characterized in that it comprises a heavy chain comprising the three CDRs of sequence SEQ ID Nos. 2, 4 and 6, or three CDRs of sequence respectively having at least 80% of identity after optimum alignment with the sequence SEQ ID Nos. 2, 4 and 6 and in that it moreover comprises a light chain comprising the three CDRs of sequence SEQ ID Nos. 1, 3 and 5, or three CDRs of sequence respectively having at least 80% of identity after optimum alignment with the sequence SEQ ID Nos. 1, 3 and 5.

As state in the art, it is known that the largest variability (length and composition) between the 6 CDRs is observed for the 3 CDRs of the heavy chain and, more particularly, the CDR-H3. As a consequence, it will be understand that the preferential characteristic CDR of the antibody of the invention is the 3 CDRs of the heavy chain, i.e. CDRs coded by sequence SEQ ID Nos. 2, 4 and 6 and, more preferentially, the CDR corresponding to CDR-H3 coded by SEQ ID No. 6.

According to another aspect, a subject of the present invention is an antibody or one of its functional fragments, according to the invention, characterized in that it does not attach or it does not attach in a significant manner to the human insulin receptor IR.

In a preferred manner, said functional fragments according to the present invention will be chosen from the fragments Fv, scFv, Fab, $(Fab')_2$, Fab', scFv-Fc or diabodies, or any functional fragment whose half-life would have been increased by a chemical modification, especially by PEGylation, or by incorporation in a liposome.

According to another aspect, the invention relates to a murine hybridoma capable of secreting a monoclonal antibody according to the present invention, especially the hybridoma of murine origin such as deposited at the Centre National de Culture De Microorganisme (CNCM, National Center of Microorganism Culture) (Institut Pasteur, Paris, France) on Jun. 23, 2005 under the number I-3466, said hybridoma resulting from the fusion of Balb/c splenocytes of immunized mice and Sp2O Ag 14 myeloma cell lines.

The monoclonal antibody here called I-3466, or one of its functional fragments, characterized in that said antibody is secreted by the hybridoma deposited at the CNCM on Jun. 23, 2005 under the number I-3466 is, of course, part of the present invention.

In a particular embodiment, the present invention relates to a murine antibody, or one of its functional fragments, according to the invention, characterized in that said antibody comprises a light chain of sequence comprising the amino acid sequence SEQ ID No. 7, or a sequence having at least 80% identity after optimum alignment with the sequence SEQ ID No. 7, or/and in that it comprises a heavy chain of sequence comprising the amino acid sequence SEQ ID No. 8, or a sequence having at least 80% identity after optimum alignment with the sequence SEQ ID No. 8.

According to a likewise particular aspect, the present invention relates to a chimeric antibody, or one of its functional fragments, according to the invention, characterized in that said antibody moreover comprises the light chain and heavy chain constant regions derived from an antibody of a species heterologous to the mouse, especially man, and in a preferred manner in that the light chain and heavy chain constant regions derived from a human antibody are respectively the kappa and gamma-1, gamma-2 or gamma-4 region.

In a particular embodiment corresponding to the isotype $IgG_1$, a supplementary characteristic of the antibody is to potentially display effector functions as ADCC (for Antibody Dependent Cellular Cytotoxicity) and/or CDC (for Complement Dependent Cytotoxicity).

According to a likewise particular aspect, the present invention relates to a humanized antibody or one of its functional fragments, according to the invention, characterized in that said antibody comprises a light chain and/or a heavy chain in which the skeleton segments FR1 to FR4 of said light chain and/or heavy chain are respectively derived from skeleton segments FR1 to FR4 of human antibody light chain and/or heavy chain.

According to a preferred embodiment, the humanized antibody or one of its functional fragments, according to the present invention is characterized in that said humanized antibody comprises a light chain comprising the amino acid sequence SEQ ID No. 17, or a sequence having at least 80% identity after optimum alignment with the sequence SEQ ID No. 17, or/and in that it comprises a heavy chain comprising the amino acid sequence SEQ ID No. 18, or a sequence having at least 80% identity after optimum alignment with the sequence SEQ ID No. 18.

Preferably, the humanized antibody, or one of its functional fragments, according to the invention is characterized in that said humanized antibody comprises a light chain comprising the amino acid sequence SEQ ID No. 17 and in that it comprises a heavy chain of sequence comprising the amino acid sequence SEQ ID No. 18.

According to a novel aspect, the present invention relates to an isolated nucleic acid, characterized in that it is chosen from the following nucleic acids:

a) a nucleic acid, DNA or RNA, coding for an antibody, or one of its functional fragments, according to the invention;
b) a complementary nucleic acid of a nucleic acid such as defined in a);
c) a nucleic acid of at least 18 nucleotides capable of hybridizing under conditions of great stringency with at least one of the CDRs of nucleic acid sequence SEQ ID No. 9, 10, 11, 12, 13 or 14, or with a sequence having at least 80%, preferably 85%, 90%, 95% and 98%, identity after optimum alignment with the sequence SEQ ID No. 9, 10, 11, 12, 13 or 14;
d) a nucleic acid of at least 18 nucleotides capable of hybridizing under conditions of great stringency with at least the light chain of nucleic acid sequence SEQ ID No. 15 and/or the heavy chain of nucleic acid sequence SEQ ID No. 16, or with a sequence having at least 80%, preferably 85%, 90%, 95% and 98%, identity after optimum alignment with the sequence SEQ ID No. 15 and/or 16;
e) a nucleic acid of at least 18 nucleotides capable of hybridizing under conditions of great stringency with at least the light chain of nucleic acid sequence SEQ ID No. 19 and/or the heavy chain of nucleic acid sequence SEQ ID No. 20, or with a sequence having at least 80%, preferably 85%, 90%, 95% and 98%, identity after optimum alignment with the sequence SEQ ID No. 19 and/or 20.

By nucleic acid, nucleic or nucleic acid sequence, polynucleotide, oligonucleotide, polynucleotide sequence, nucleotide sequence, terms which will be employed indifferently in the present specification, it is intended to indicate a precise linkage of nucleotides, which are modified or unmodified, allowing a fragment or a region of a nucleic acid to be defined, containing or not containing unnatural nucleotides, and being able to correspond just as well to a double-stranded DNA, a single-stranded DNA as to the transcription products of said DNAs.

It must also be understood here that the present invention does not concern the nucleotide sequences in their natural chromosomal environment, that is to say in the natural state. It concerns sequences which have been isolated and/or purified, that is to say that they have been selected directly or indirectly, for example by copy, their environment having been at least partially modified. It is thus likewise intended to indicate here the isolated nucleic acids obtained by genetic recombination by means, for example, of host cells or obtained by chemical synthesis.

By nucleic sequences having a percentage of identity of at least 80%, preferably 85%, 90%, 95% and 98%, after optimum alignment with a preferred sequence, it is intended to indicate the nucleic sequences having, with respect to the reference nucleic sequence, certain modifications such as, in particular, a deletion, a truncation, an elongation, a chimeric fusion and/or a substitution, especially point substitution. It preferably concerns sequences in which the sequences code for the same amino acid sequences as the reference sequence, this being connected to the degeneracy of the genetic code, or complementary sequences which are capable of hybridizing specifically with the reference sequences, preferably under conditions of high stringency, especially such as defined below.

A hybridization under conditions of high stringency signifies that the temperature conditions and ionic strength conditions are chosen in such a way that they allow the maintenance of the hybridization between two fragments of complementary DNA. By way of illustration, conditions of high stringency of the hybridization step for the purposes of defining the polynucleotide fragments described above are advantageously the following.

The DNA-DNA or DNA-RNA hybridization is carried out in two steps: (1) prehybridization at 42° C. for 3 hours in phosphate buffer (20 mM, pH 7.5) containing 5×SSC (1×SSC corresponds to a 0.15 M NaCl+0.015 M sodium citrate solution), 50% of formamide, 7% of sodium dodecyl sulfate (SDS), 10×Denhardt's, 5% of dextran sulfate and 1% of salmon sperm DNA; (2) actual hybridization for 20 hours at a temperature dependent on the size of the probe (i.e.: 42° C. for a probe size>100 nucleotides) followed by 2 washes of 20 minutes at 20° C. in 2×SSC+2% of SDS, 1 wash of 20 minutes at 20° C. in 0.1×SSC+0.1% of SDS. The last wash is carried out in 0.1×SSC+0.1% of SDS for 30 minutes at 60° C. for a probe size>100 nucleotides. The hybridization conditions of high stringency described above for a polynucleotide of defined size can be adapted by the person skilled in the art for oligonucleotides of greater or smaller size, according to the teaching of Sambrook et al., (1989, Molecular cloning: a laboratory manual. 2nd Ed. Cold Spring Harbor).

The invention likewise relates to a vector comprising a nucleic acid according to the present invention.

The invention aims especially at cloning and/or expression vectors which contain a nucleotide sequence according to the invention.

The vectors according to the invention preferably contain elements which allow the expression and/or the secretion of the nucleotide sequences in a determined host cell. The vector must therefore contain a promoter, signals of initiation and termination of translation, as well as appropriate regions of regulation of transcription. It must be able to be maintained in a stable manner in the host cell and can optionally have particular signals which specify the secretion of the translated protein. These different elements are chosen and optimized by the person skilled in the art as a function of the host cell used. To this effect, the nucleotide sequences according to the invention can be inserted into autonomous replication vectors in the chosen host, or be integrative vectors of the chosen host.

Such vectors are prepared by methods currently used by the person skilled in the art, and the resulting clones can be introduced into an appropriate host by standard methods, such as lipofection, electroporation, thermal shock, or chemical methods.

The vectors according to the invention are, for example, vectors of plasmidic or viral origin. They are useful for transforming host cells in order to clone or to express the nucleotide sequences according to the invention.

The invention likewise comprises the host cells transformed by or comprising a vector according to the invention.

The host cell can be chosen from prokaryotic or eukaryotic systems, for example bacterial cells but likewise yeast cells or animal cells, in particular mammalian cells. It is likewise possible to use insect cells or plant cells.

The invention likewise concerns animals, except man, which comprise at least one cell transformed according to the invention.

According to another aspect, a subject of the invention is a process for production of an antibody, or one of its functional fragments according to the invention, characterized in that it comprises the following stages:

a) culture in a medium and appropriate culture conditions of a host cell according to the invention; and
b) the recovery of said antibodies, or one of their functional fragments, thus produced starting from the culture medium or said cultured cells.

The cells transformed according to the invention can be used in processes for preparation of recombinant polypeptides according to the invention. The processes for preparation of a polypeptide according to the invention in recombinant form, characterized in that they employ a vector and/or a cell transformed by a vector according to the invention, are themselves comprised in the present invention. Preferably, a cell transformed by a vector according to the invention is cultured under conditions which allow the expression of said polypeptide and said recombinant peptide is recovered.

As has been said, the host cell can be chosen from prokaryotic or eukaryotic systems. In particular, it is possible to identify nucleotide sequences according to the invention, facilitating secretion in such a prokaryotic or eukaryotic system. A vector according to the invention carrying such a sequence can therefore advantageously be used for the production of recombinant proteins, intended to be secreted. In effect, the purification of these recombinant proteins of interest will be facilitated by the fact that they are present in the supernatant of the cell culture rather than in the interior of the host cells.

It is likewise possible to prepare the polypeptides according to the invention by chemical synthesis. Such a preparation process is likewise a subject of the invention. The person skilled in the art knows the processes of chemical synthesis, for example the techniques employing solid phases (see especially Steward et al., 1984, Solid phase peptide synthesis, Pierce Chem. Company, Rockford, 111, 2nd ed., (1984)) or techniques using partial solid phases, by condensation of fragments or by a classical synthesis in solution. The polypeptides obtained by chemical synthesis and being able to contain corresponding unnatural amino acids are likewise comprised in the invention.

The antibodies, or one of their functional fragments, capable of being obtained by a process according to the invention are likewise comprised in the present invention.

According to a second embodiment, the present invention concerns an antibody according to the invention such as described further above, characterized in that it is, moreover, capable of binding specifically to a human receptor of the tyrosine kinase family and/or capable of inhibiting the tyrosine kinase activity of such receptor.

In a first embodiment, such an antibody consists in a bispecific antibody comprising a second motif capable of specifically inhibiting the binding of EGF on the human epidermal growth factor receptor (EGFR) and/or inhibiting the tyrosine kinase activity of said EGFR. In a more preferred embodiment of the invention, said second anti-EGFR motif is issued from the murine monoclonal antibody 225, its chimeric derivative C225 or any humanized antibody derived from this antibody 225.

In a second embodiment, such an antibody consists in a bispecific antibody comprising a second motif capable of specifically inhibiting the activity modulated by the HER2/neu receptor and/or inhibiting the tyrosine kinase activity of said HER2/neu receptor. In a more preferred embodiment of the invention, said second anti-HER2/neu motif is issued from the murine monoclonal antibody 4D5 or 2C4 or the humanized antibody Trastuzumab or Pertuzumab.

In a third embodiment, such an antibody consists in a bispecific antibody comprising a second motif capable of specifically inhibiting the binding of the Hepatocyte Growth Factor (HGF) on the cMET receptor and/or specifically inhibiting the tyrosine kinase activity of said cMET receptor.

Finally, in a last embodiment, such an antibody consists in a bispecific antibody comprising a second motif capable of specifically inhibiting the binding of the Macrophage Stimulating Protein (MSP) on the RON receptor and/or inhibiting the tyrosine kinase activity of said RON receptor.

According to another embodiment of the invention, it is also considered that the antibody according to the invention is capable to interact with any kind of receptor being implicated in the development of tumors such as, for example, without limitation, VEGFR, FGF (Fibroblast Growth Factor), PDGF (Platelet derived growth factor) or CXCR4 or 2 (Chemokine receptor type 4 or 2).

The bispecific or bifunctional antibodies form a second generation of monoclonal antibodies in which two different variable regions are combined in the same molecule (Hollinger and Bohlen, 1999, Cancer and metastasis, rev. 18:411-419). Their use has been demonstrated both in the diagnostic field and in the therapy field from their capacity to recruit new effector functions or to target several molecules on the surface of tumor cells. These antibodies can be obtained by chemical methods (Glennie M J et al., 1987, J. Immunol., 139, 2367-2375; Repp R. et al., 1995, J. Hemat., 377-382) or somatic methods (Staerz U. D. and Bevan M. J., 1986, PNAS 83, 1453-1457; Suresh M. R. et al., 1986, Method Enzymol., 121:210-228) but likewise and preferentially by genetic engineering techniques which allow the heterodimerization to be forced and thus facilitate the process of purification of the antibody sought (Merchand et al., 1998 Nature Biotech., 16:677-681).

These bispecific antibodies can be constructed as entire IgG, as bispecific Fab'2, as Fab'PEG or as diabodies or else as bispecific scFv but likewise as a tetravalent bispecific antibody or two attachment sites are present for each antigen targeted (Park et al., 2000, Mol. Immunol., 37 (18):1123-30) or its fragments as described further above.

In addition to an economic advantage from the fact that the production and the administration of a bispecific antibody are less onerous than the production of two specific antibodies, the use of such bispecific antibodies has the advantage of reducing the toxicity of the treatment. This is because the use of a bispecific antibody allows the total quantity of circulating antibodies to be reduced and, consequently, the possible toxicity.

In a preferred embodiment of the invention, the bispecific antibody is a bivalent or tetravalent antibody.

The invention likewise concerns a pharmaceutical composition comprising by way of active principle a compound consisting of an antibody, or one of its functional fragments according to the invention, preferably mixed with an excipient and/or a pharmaceutically acceptable vehicle.

According to yet another embodiment, the present invention likewise concerns a pharmaceutical composition such as described further above which comprises at least a second compound chosen from the compounds capable of specifically inhibiting the tyrosine kinase activity of IGF-IR, EGFR, HER2/neu, VEGFR, cMET and/or RON.

In a second preferred aspect of the invention, said second compound is chosen from the isolated anti-EGFR, -IGF-IR, -HER2/neu, anti-VEGFR, -cMET and/or -RON antibodies, or their functional fragments, capable of inhibiting the proliferative and/or anti-apoptotic and/or angiogenic and/or metastatic dissemination inductor activity mediated by said receptor(s).

According to another embodiment of the invention, the composition comprises, as combination product for a simultaneous, separate or sequential use, at least an inhibitor of the tyrosine kinase activity of the IGF-IR, EGFR, HER2/neu, VEGFR, cMET and/or RON.

In another preferred embodiment, said inhibitor of the tyrosine kinase activity of the receptors is selected from the group consisting of derived natural agents, dianilinophthalimides, pyrazolo- or pyrrolopyridopyrimidines or else quinazilines. Such inhibitory agents are well known to the person skilled in the art and described in the literature (Ciardiello F., Drugs 2000, Suppl. 1, 25-32).

Another complementary embodiment of the invention consists in a composition such as described above which comprises, moreover, as a combination product for simultaneous, separate or sequential use, a cytotoxic/cytostatic agent.

"Simultaneous use" is understood as meaning the administration of the two compounds of the composition according to the invention in a single and identical pharmaceutical form.

"Separate use" is understood as meaning the administration, at the same time, of the two compounds of the composition according to the invention in distinct pharmaceutical forms.

"Sequential use" is understood as meaning the successive administration of the two compounds of the composition according to the invention, each in a distinct pharmaceutical form.

In a general fashion, the composition according to the invention considerably increases the efficacy of the treatment of cancer. In other words, the therapeutic effect of the anti-IGF-IR antibody according to the invention is potentiated in an unexpected manner by the administration of a cytotoxic agent. Another major subsequent advantage produced by a composition according to the invention concerns the possibility of using lower efficacious doses of active principle, which allows the risks of appearance of secondary effects to be avoided or to be reduced, in particular the effects of the cytotoxic agent.

In addition, this composition according to the invention would allow the expected therapeutic effect to be attained more rapidly.

By "anti-cancer therapeutic agents" or "cytotoxic agents", it is intended a substance which, when administered to a subject, treats or prevents the development of cancer in the subject's body. As non limitative example of such agents, it can be mentioned alkylating agents, anti-metabolites, anti-tumor antibiotics, mitotic inhibitors, chromatin function inhibitors, anti-angiogenesis agents, anti-estrogens, anti-androgens or immunomodulators.

Such agents are, for example, cited in the 2001 edition of VIDAL, on the page devoted to the compounds attached to the cancerology and hematology column "Cytotoxics", these cytotoxic compounds cited with reference to this document are cited here as preferred cytotoxic agents.

More particularly, the following agents are preferred according to the invention.

"Alkylating agent" refers to any substance which can cross-link or alkylate any molecule, preferably nucleic acid (e.g., DNA), within a cell. Examples of alkylating agents include nitrogen mustard such as mechlorethamine, chlorambucol, melphalen, chlorydrate, pipobromen, prednimustin, disodic-phosphate or estramustine; oxazophorins such as cyclophosphamide, altretamine, trofosfamide, sulfofosfamide or ifosfamide; aziridines or imine-ethylenes such as thiotepa, triethylenamine or altetramine; nitrosourea such as carmustine, streptozocin, fotemustin or lomustine; alkylesulfonates such as busulfan, treosulfan or improsulfan; triazenes such as dacarbazine; or platinum complexes such as cis-platinum, oxaliplatin and carboplatin.

"Anti-metabolites" refer to substances that block cell growth and/or metabolism by interfering with certain activities, usually DNA synthesis. Examples of anti-metabolites include methotrexate, 5-fluoruracil, floxuridine, 5-fluorodeoxyuridine, capecitabine, cytarabine, fludarabine, cytosine arabinoside, 6-mercaptopurine (6-MP), 6-thioguanine (6-TG), chlorodesoxyadenosine, 5-azacytidine, gemcitabine, cladribine, deoxycoformycin and pentostatin.

"Anti-tumor antibiotics" refer to compounds which may prevent or inhibit DNA, RNA and/or protein synthesis. Examples of anti-tumor antibiotics include doxorubicin, daunorubicin, idarubicin, valrubicin, mitoxantrone, dactinomycin, mithramycin, plicamycin, mitomycin C, bleomycin, and procarbazine.

"Mitotic inhibitors" prevent normal progression of the cell cycle and mitosis. In general, microtubule inhibitors or taxoides such as paclitaxel and docetaxel are capable of inhibiting mitosis. Vinca alkaloid such as vinblastine, vincristine, vindesine and vinorelbine are also capable of inhibiting mitosis.

"Chromatin function inhibitors" or "topoisomerase inhibitors" refer to substances which inhibit the normal function of chromatin modeling proteins such as topoisomerase I or topoisomerase II. Examples of chromatin function inhibitors include, for topoisomerase I, camptothecine and its derivatives such as topotecan or irinotecan, and, for topoisomerase II, etoposide, etoposide phosphate and teniposide.

"Anti-angiogenesis agent" refers to any drug, compound, substance or agent which inhibits growth of blood vessels. Exemplary anti-angiogenesis agents include, but are by no means limited to, razoxin, marimastat, batimastat, prinomastat, tanomastat, ilomastat, CGS-27023A, halofuginon, COL-3, neovastat, BMS-275291, thalidomide, CDC 501, DMXAA, L-651582, squalamine, endostatin, SU5416, SU6668, interferon-alpha, EMD121974, interleukin-12, IM862, angiostatin and vitaxin.

"Anti-estrogen" or "anti-estrogenic agent" refer to any substance which reduces, antagonizes or inhibits the action of estrogen. Examples of anti-estrogen agents are tamoxifen, toremifene, raloxifene, droloxifene, iodoxyfene, anastrozole, letrozole, and exemestane.

"Anti-androgens" or "anti-androgen agents" refer to any substance which reduces, antagonizes or inhibits the action of an androgen. Examples of anti-androgens are flutamide, nilutamide, bicalutamide, sprironolactone, cyproterone acetate, finasteride and cimitidine.

"Immunomodulators" are substances which stimulate the immune system.

Examples of immunomodulators include interferon, interleukin such as aldesleukine, OCT-43, denileukin diflitox and interleukin-2, tumoral necrose fators such as tasonermine or others immunomodulators such as lentinan, sizofuran, roquinimex, pidotimod, pegademase, thymopentine, poly I:C or levamisole in conjunction with 5-fluorouracil.

For more detail, the man skill in the art could refer to the manual edited by the "Association Française des Enseignants de Chimie Thérapeutique" and entitled "traité de chimie thérapeutique, vol. 6, Médicaments antitumoraux et perspectives dans le traitement des cancers, edition TEC & DOC, 2003".

In a particularly preferred embodiment, said composition as a combination product according to the invention is characterized in that said cytotoxic agent is coupled chemically to said antibody for simultaneous use.

In a particularly preferred embodiment, said composition according to the invention is characterized in that said cytotoxic/cytostatic agent is chosen from the spindle inhibitor or stabilizer agents, preferably vinorelbine and/or vinflunine and/or vincristine.

In order to facilitate the coupling between said cytotoxic agent and said antibody according to the invention, it is especially possible to introduce spacer molecules between the two compounds to be coupled, such as poly(alkylene)glycols like polyethylene glycol, or else amino acids, or, in another embodiment, to use active derivatives of said cytotoxic agents into which would have been introduced functions capable of reacting with said antibody according to the invention. These coupling techniques are well known to the person skilled in the art and will not be expanded upon in the present description.

Other inhibitors of EGFR can, without any limitation, consist of the anti-EGFR monoclonal antibodies C225 and 22Mab (ImClone Systems Incorporated), ABX-EGF (Abgenix/Cell Genesys), EMD-7200 (Merck KgaA) or the compounds ZD-1834, ZD-1838 and ZD-1839 (AstraZeneca), PIU-166 (Novartis), PKI-166/CGP-75166 (Novartis), PTK 787 (Novartis), CP 701 (Cephalon), leflunomide (Pharmacia/Sugen), CI-1033 (Warner-Lambert Parke-Davis), CI-1033/PD 183, 805 (Warner-Lambert Parke-Davis), CL-387, 785 (Wyeth-Ayerst), BBR-1611 (Boehringer Mannheim GmbH/Roche), Naamidine A (Bristol-Myers Squibb), RC-3940-II (Pharmacia), BIBX-1382 (Boehringer Ingelheim), OLX-103 (Merck & Co), VRCTC-310 (Ventech Research), EGF fusion toxin (Seragen Inc.), DAB-389 (Seragen/Lilgand), ZM-252808 (Imperial Cancer Research Fund), RG-50864 (INSERM), LFM-Al2 (Parker Hughes Cancer Center), WHI-P97 (Parker Hughes Cancer Center), GW-282974 (Glaxo), KT-8391 (Kyowa Hakko) or the "EGFR Vaccine" (York Medical/Centro de Immunologia Molecular).

According to yet another embodiment of the invention, the composition such as described above can likewise comprise another antibody compound directed against the extracellular domain of the HER2/neu receptor, as a combination product for simultaneous, separate or sequential use, intended for the prevention and for the treatment of cancer, especially the cancers overexpressing said HER2/neu receptor and the receptor IGF-IR and/or EGFR, such as especially cancer of the breast.

Reference can be made especially to the publications of Albanell et al. (J. of the National Cancer Institute, 93(24): 1830-1831, 2001) and of Lu et al. (J. of the National Cancer Institute, 93(24):1852-1857, 2001) justifying the unexpected interest in combining an anti-HER2/neu antibody with an anti-IGF-IR antibody according to the present invention.

In a particular manner, said anti-HER2/neu antibody of the composition according to the invention is the antibody called Trastuzumab (also called Herceptin).

The invention relates, in another aspect, to a composition characterized in that one, at least, of said antibodies, or one of their functional fragments, is conjugated with a cell toxin and/or a radioelement.

Preferably, said toxin or said radioelement is capable of inhibiting at least one cell activity of cells expressing the IGF-IR, in a more preferred manner capable of preventing the growth or the proliferation of said cell, especially of totally inactivating said cell.

Preferably also, said toxin is an enterobacterial toxin, especially Pseudomonas exotoxin A.

The radioelements (or radioisotopes) preferably conjugated to the antibodies employed for the therapy are radioisotopes which emit gamma rays and preferably iodine$^{131}$, yttrium$^{90}$, gold$^{199}$, palladium$^{100}$, copper$^{67}$, bismuth$^{217}$ and antimony$^{211}$. The radioisotopes which emit beta and alpha rays can likewise be used for the therapy.

By toxin or radioelement conjugated to at least one antibody, or one of its functional fragments, according to the invention, it is intended to indicate any means allowing said toxin or said radioelement to bind to said at least one antibody, especially by covalent coupling between the two compounds, with or without introduction of a linking molecule.

Among the agents allowing binding in a chemical (covalent), electrostatic or noncovalent manner of all or part of the components of the conjugate, mention may particularly be made of benzoquinone, carbodiimide and more particularly EDC (1-ethyl-3-[3-dimethylaminopropyl]-carbodiimide hydrochloride), dimaleimide, dithiobis-nitrobenzoic acid (DTNB), N-succinimidyl S-acetyl thio-acetate (SATA), the bridging agents having one or more phenylazide groups reacting with the ultraviolets (U.V.) and preferably N-[-4-(azidosalicylamino)butyl]-3'-(2'-pyridyldithio)propionamide (APDP), N-succinimid-yl 3-(2-pyridyldithio)propionate (SPDP), 6-hydrazino-nicotinamide (HYNIC).

Another form of coupling, especially for the radioelements, can consist in the use of a bifunctional ion chelator.

Among these chelates, it is possible to mention the chelates derived from EDTA (ethylenediaminetetraacetic acid) or from DTPA (diethylenetriaminepentaacetic acid) which have been developed for binding metals, especially radioactive metals, and immunoglobulins. Thus, DTPA and its derivatives can be substituted by different groups on the carbon chain in order to increase the stability and the rigidity of the ligand-metal complex (Krejcarek et al., 1977; Brechbiel et al., 1991; Gansow, 1991; U.S. Pat. No. 4,831,175).

For example diethylenetriaminepentaacetic acid (DTPA) and its derivatives, which have been widely used in medicine and in biology for a long time either in their free form, or in the form of a complex with a metallic ion, have the remarkable characteristic of forming stable chelates with metallic ions and of being coupled with proteins of therapeutic or diagnostic interest such as antibodies for the development of radioimmunoconjugates in cancer therapy (Meases et al., 1984; Gansow et al., 1990).

Likewise preferably, said at least one antibody forming said conjugate according to the invention is chosen from its functional fragments, especially the fragments amputated of their Fc component such as the scFv fragments.

The present invention moreover comprises the use of the composition according to the invention for the preparation of a medicament.

More particularly, according to another embodiment, the invention concerns the use of an antibody, or one of its functional fragments, and/or of a composition for the preparation of a medicament intended for the prevention or for the treatment of an illness induced by an overexpression and/or an abnormal activation of the IGF-IR, and/or connected with a hyperactivation of the transduction pathway of the signal mediated by the interaction of the IGF1 or IGF2 with IGF-IR.

According to yet another preferred embodiment, the invention concerns the use of an antibody, or one of its functional fragments, and/or of a composition for the preparation of a medicament intended for the prevention or for the treatment of an illness induced by an overexpression and/or an abnormal activation of the IGF-IR, and/or connected with a hyperactivation of the transduction pathway of the signal mediated by the interaction of the IGF2 with IGF-IR.

Preferably, said use according to the invention is characterized in that the administration of said medicament does not induce or induces only slightly secondary effects connected with inhibition of the insulin receptor IR, that is to say inhibition of the interaction of the IR with its natural ligands due to the presence of said medicament, especially by a competitive inhibition connected with the attachment of said medicament to the IR.

The present invention moreover comprises the use of an antibody, or one of its functional fragments, preferably humanized, and/or of a composition according to the invention for the preparation of a medicament intended to inhibit the transformation of normal cells into cells with tumoral character, preferably IGF-dependent, especially at least IGF2-dependent cells.

The present invention likewise relates to the use of an antibody, or one of its functional fragments, preferably humanized, and/or of a composition according to the invention for the preparation of a medicament intended to inhibit the growth and/or the proliferation of tumor cells, preferably IGF-dependent, especially at least IGF2-dependent cells.

In a general manner, a subject of the present invention is the use of an antibody, or one of its functional fragments, preferably humanized, and/or of a composition according to the invention, for the preparation of a medicament intended for the prevention or for the treatment of cancer preferably expressing IGF-IR, and/or of cancer preferably having a hyperactivation of the transduction pathway of the signal mediated by the interaction of IGF1 and/or IGF2 with IGF-IR, such as, for example, the overexpression of IRS1.

The subject of the present invention is likewise the use of an antibody, or one of its functional fragments, preferably humanized, and/or of a composition according to the invention, for the preparation of a medicament intended for the prevention or for the treatment of psoriasis, psoriasis whose epidermal hyperproliferation can be connected with the expression or the overexpression of IGF-IR, and/or with the hyperactivation of the transduction pathway of the signal mediated by the interaction of IGF-IR with its natural ligands (Wraight C. J. et al., Nat. Biotechnol., 2000, 18(5):521-526, Reversal of epidermal hyperproliferation in psoriasis by insulin-like growth factor I receptor antisense oligonucleotides) and/or of EGFR with its natural ligands.

The invention also relates to the use of the antibody, or any functional fragments thereof, preferentially humanized, and/or of any composition comprising said antibody, for the preparation of a medicament for the treatment or the prevention of atherosclerosis.

Among the cancers which can be prevented and/or treated, prostate cancer, osteosarcomas, lung cancer, breast cancer, endometrial cancer, colon cancer, multiple myeloma or ovary cancer or any other cancer overexpressing IGF-IR is preferred.

In a more preferred embodiment, due to the particular ability to displace IGF2, the invention relates to the use of the antibody, or fragment thereof, according to the invention, for the prevention, diagnostic or treatment of colon cancer, as IGF2 is known to be particularly implicated in this cancer.

According to yet another aspect, a subject of the present invention is a method of diagnosis, preferably in vitro, of illnesses connected with an overexpression or an underexpression, preferably an overexpression, of the IGF-IR starting from a biological sample in which the abnormal presence of IGF-IR is suspected, characterized in that said biological sample is contacted with an antibody, or one of its functional fragments, according to the invention, it being possible for said antibody to be, if necessary, labeled.

Preferably, said illnesses connected with the overexpression of the IGF-IR in said diagnosis method will be cancers.

Said antibody, or one of its functional fragments, can be present in the form of an immunoconjugate or of a labeled antibody so as to obtain a detectable and/or quantifiable signal.

An object of the invention is a method of in vitro diagnosis of pathological condition characterized by aberrant expression of IGF-IR relative to normal, said method comprising contacting a biological sample suspected of containing IGF-IR, with the antibody according the invention, under conditions favoring formation of an IGF-IR/antibody complex, and detecting said complex as indicating presence said IGF-IR in said sample. In a preferred embodiment, said antibody is detectably labeled.

In a first aspect, the aberrant expression of IGF-IR is an over-expression of IGF-IR. In a second aspect, the aberrant expression of IGF-IR is an under-expression of IGF-IR.

The antibodies labeled according to the invention or their functional fragments include, for example, antibodies called immunoconjugates which can be conjugated, for example, with enzymes such as peroxidase, alkaline phosphatase, α-D-galactosidase, glucose oxydase, glucose amylase, carbonic anhydrase, acetylcholinesterase, lysozyme, malate dehydrogenase or glucose 6-phosphate dehydrogenase or by a molecule such as biotin, digoxygenin or 5-bromodeoxyuridine. Fluorescent labels can be likewise conjugated to the antibodies or to their functional fragments according to the invention and especially include fluorescein and its derivatives, fluorochrome, rhodamine and its derivatives, GFP (GFP for "Green Fluorescent Protein"), dansyl, umbelliferone etc. In such conjugates, the antibodies of the invention or their functional fragments can be prepared by methods known to the person skilled in the art. They can be coupled to the enzymes or to the fluorescent labels directly or by the intermediary of a spacer group or of a linking group such as a polyaldehyde, like glutaraldehyde, ethylenediaminetetraacetic acid (EDTA), diethylene-triaminepentaacetic acid (DPTA), or in the presence of coupling agents such as those mentioned above for the therapeutic conjugates. The conjugates containing labels of fluorescein type can be prepared by reaction with an isothiocyanate.

Other conjugates can likewise include chemo luminescent labels such as luminol and the dioxetanes, bio-luminescent labels such as luciferase and luciferin, or else radioactive labels such as iodine$^{123}$, iodine$^{125}$, iodine$^{126}$, iodine$^{133}$, bromine$^{77}$, technetium$^{99m}$, indium$^{111}$, indium$^{113m}$, gallium$^{67}$, gallium$^{68}$, ruthenium$^{95}$, ruthenium$^{97}$, ruthenium$^{103}$, ruthenium$^{105}$, mercury$^{107}$, mercury$^{203}$, rhenium$^{99m}$, rhenium$^{101}$, rhenium$^{105}$, scandium$^{47}$, tellurium$^{121m}$, tellurium$^{122m}$, tellurium$^{125m}$, thulium$^{165}$, thulium$^{167}$, thulium$^{168}$, fluorine$^{18}$, yttrium$^{199}$, iodine$^{131}$. The methods known to the person skilled in the art existing for coupling the therapeutic radio-isotopes to the antibodies either directly or via a chelating agent such as EDTA, DTPA mentioned above can be used for the radioelements which can be used in diagnosis. It is likewise possible to mention labeling with Na[I$^{125}$] by the chloramine T method [Hunter W. M. and Greenwood F. C. (1962) Nature 194:495] or else with technetium$^{99m}$ by the technique of Crockford et al. (U.S. Pat. No. 4,424,200) or attached via DTPA as described by Hnatowich (U.S. Pat. No. 4,479,930).

Thus, the antibodies, or their functional fragments, according to the invention can be employed in a process for the detection and/or the quantification of an overexpression or of an underexpression, preferably an overexpression, of the IGF-IR in a biological sample, characterized in that it comprises the following steps:

a) the contacting of the biological sample with an antibody, or one of its functional fragments, according to the invention; and
b) the demonstration of the IGF-IR/antibody complex possibly formed.

In a particular embodiment, the antibodies, or their functional fragments, according to the invention, can be employed in a process for the detection and/or the quantification of the IGF-IR in a biological sample, for the monitoring of the efficacy of a prophylactic and/or therapeutic treatment of IGF-dependent cancer or else of psoriasis or atherosclerosis.

More generally, the antibodies, or their functional fragments, according to the invention can be advantageously employed in any situation where the expression of the IGF-IR must be observed in a qualitative and/or quantitative manner.

Preferably, the biological sample is formed by a biological fluid, such as serum, whole blood, cells, a tissue sample or biopsies of human origin.

Another aspect of the invention is a diagnostic method for predicting an oncogenic potential of a sample of prostate cells, comprising:

(a) providing a sample of human prostate tissue; and
(b) determining, in the sample, presence of IGF-IR, said step comprising contacting said sample with the antibody according to the invention under conditions favoring formation of an IGF-IR/antibody complex, wherein presence of said complex indicates the oncogenic potential of said cells in said tissue.

In another embodiment, the presence of said complex indicates that the patient is at risk of developing or onset of a pathological disorder characterized by overexpression of said IGF-IR.

An object of the invention is also a method for following progress of a therapeutic regime designed to alleviate a pathological disorder characterized by abnormal expression of IGF-IR expression, comprising:

(a) assaying a sample from a subject to determine level of IGF-IR at a first time point;
(b) assaying said sample at a second time point; and
(c) comparing said level at said second time point to the level determined in (a) as a determination of effect of said therapeutic regime wherein a decrease in the level of IGF-IR in said sample is determinative of the regression said pathological disorder in said patient or an increase in the level of IGF-IR is determinative of the progression of said pathological disorder in said patient.

Any procedure or conventional test can be employed in order to carry out such a detection and/or dosage. Said test can be a competition or sandwich test, or any test known to the person skilled in the art dependent on the formation of an immune complex of antibody-antigen type. Following the applications according to the invention, the antibody or one of its functional fragments can be immobilized or labeled. This immobilization can be carried out on numerous supports known to the person skilled in the art. These supports can especially include glass, polystyrene, poly-propylene, polyethylene, dextran, nylon, or natural or modified cells. These supports can be either soluble or insoluble.

By way of example, a preferred method brings into play immunoenzymatic processes according to the ELISA technique, by immunofluorescence, or radio-immunoassay (RIA) technique or equivalent.

Thus, the present invention likewise comprises the kits or sets necessary for carrying out a method of diagnosis of illnesses induced by an overexpression or an underexpression of the IGF-IR or for carrying out a process for the detection and/or the quantification of an overexpression or of an underexpression of the IGF-IR in a biological sample, preferably an overexpression of said receptor, characterized in that said kit or set comprises the following elements:

a) an antibody, or one of its functional fragments, according to the invention;
b) optionally, the reagents for the formation of the medium favorable to the immunological reaction;
c) optionally, the reagents allowing the demonstration of IGF-IR/antibody complexes produced by the immunological reaction.

The invention moreover relates to the use of a composition as a combination product according to the invention, for the preparation of a medicament intended for the prevention or for the treatment of cancer, especially cancers for which said cytotoxic agent or said anti-HER2/neu antibody is generally prescribed and, especially, for which cancers the tumor cells express or overexpress the IGF-IR.

A subject of the invention is likewise the use of an antibody according to the invention for the preparation of a medicament intended for the specific targeting of a biologically active compound to cells expressing or overexpressing the IGF-IR.

It is intended here by biologically active compound to indicate any compound capable of modulating, especially of inhibiting, cell activity, in particular their growth, their proliferation, transcription or gene translation.

A subject of the invention is also an in vivo diagnostic reagent comprising an antibody according to the invention, or one of its functional fragments, preferably labeled, especially radiolabeled, and its use in medical imaging, in particular for the detection of cancer connected with the expression or the overexpression by a cell of the IGF-IR.

The invention likewise relates to a composition as a combination product or to an anti-IGF-IR/toxin conjugate or radioelement, according to the invention, as a medicament.

Preferably, said composition as a combination product or said conjugate according to the invention will be mixed with an excipient and/or a pharmaceutically acceptable vehicle.

In the present description, pharmaceutically acceptable vehicle is intended to indicate a compound or a combination of compounds entering into a pharmaceutical composition not provoking secondary reactions and which allows, for example, facilitation of the administration of the active compound(s), an increase in its lifespan and/or in its efficacy in the body, an increase in its solubility in solution or else an improvement in its conservation. These pharmaceutically acceptable vehicles are well known and will be adapted by the person skilled in the art as a function of the nature and of the mode of administration of the active compound(s) chosen.

Preferably, these compounds will be administered by the systemic route, in particular by the intravenous route, by the intramuscular, intradermal, intraperitoneal or subcutaneous route, or by the oral route. In a more preferred manner, the composition comprising the antibodies according to the invention will be administered several times, in a sequential manner.

Their modes of administration, dosages and optimum pharmaceutical forms can be determined according to the criteria generally taken into account in the establishment of a treatment adapted to a patient such as, for example, the age or the body weight of the patient, the seriousness of his/her general condition, the tolerance to the treatment and the secondary effects noted.

Other characteristics and advantages of the invention appear in the continuation of the description with the examples and the figures whose legends are represented below.

LEGENDS TO THE FIGURES

FIG. 1: Competition of [$^{125}$I]-IGF-1 binding to IGF-IR by the monoclonal antibody I-3466.

Specific [$^{125}$I]-IGF-1 binding (in %) was plotted as a function of ligand concentration on a semilog graph. Specific binding values are the means of experiments performed in triplicate.

Figure 2:
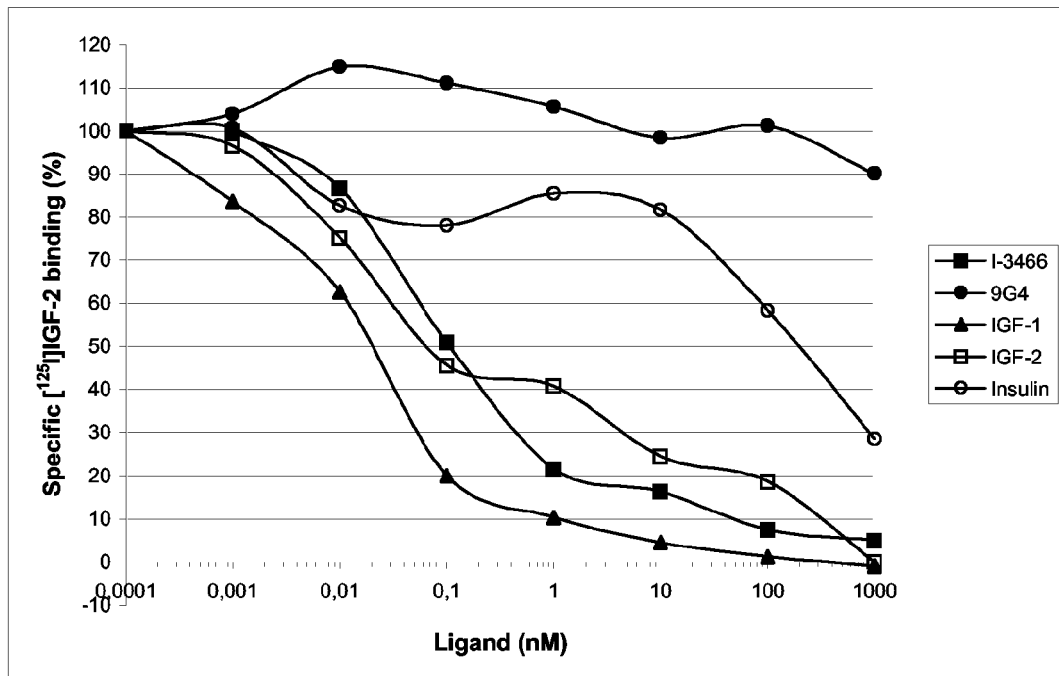

FIG. 2: Competition of [$^{125}$I]-IGF-2 binding to IGF-IR by the monoclonal antibody I-3466.

Specific [$^{125}$I]-IGF-2 binding (in %) was plotted as a function of ligand concentration on a semilog graph. Specific binding values are the means of experiments performed in triplicate.

Figures 3A, 3B:
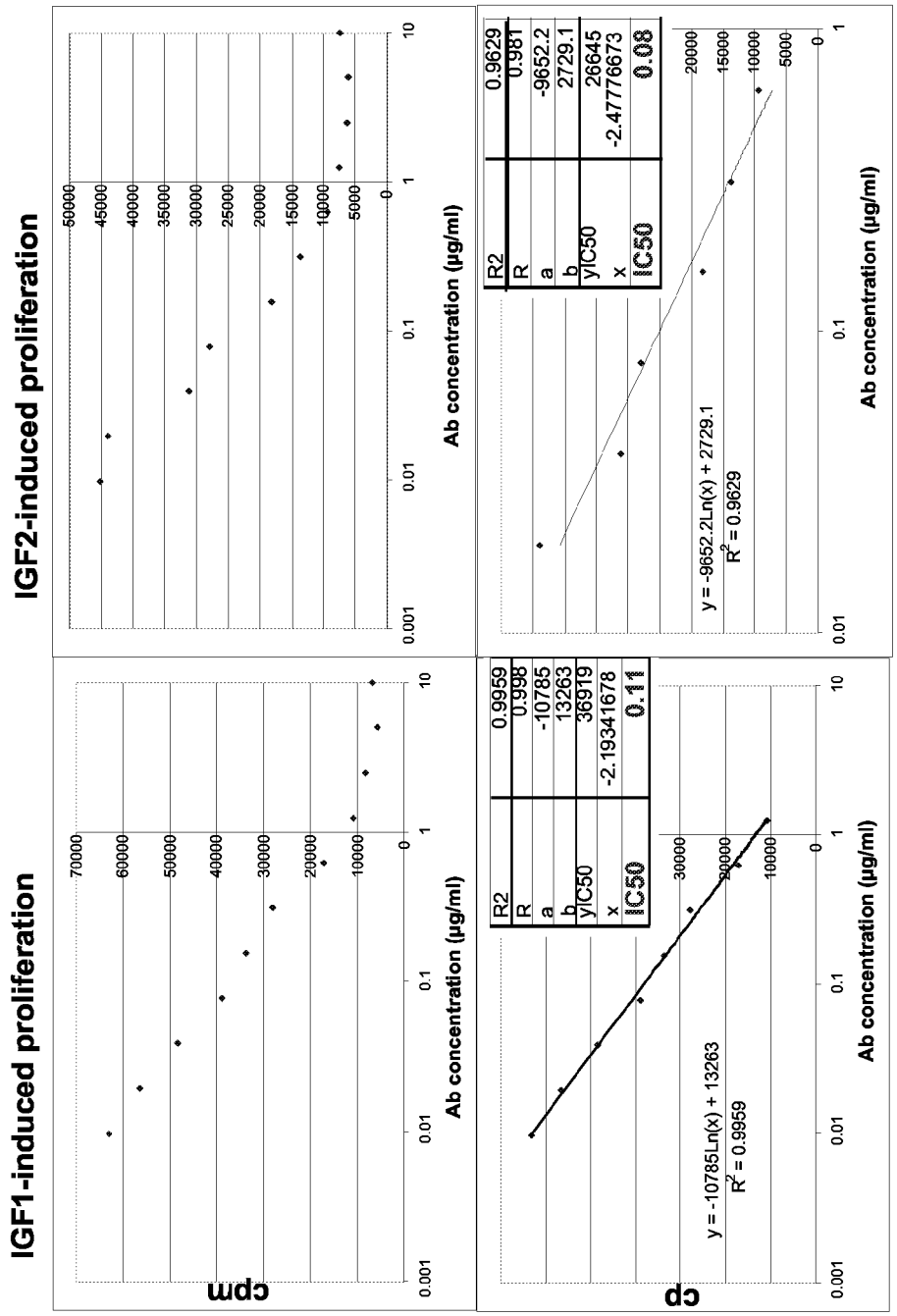

FIGS. 3A and 3B: In vitro effect of the I-3466 antibody on either IGF1- or IGF2-induced MCF-7 growth.

FIGS. 4A and 4B: Effect of the I-3466 Mab on either IGF1 (FIG. 4A) or IGF2 (FIG. 4B)-*induced* phosphorylation of IGF-IR β-chain on MCF-7 cells.

FIGS. 5A and 5B: Effect of the I-3466 Mab on either IGF1 (FIG. 5A) or IGF2 (FIG. 5B)-*induced* phosphorylation of IGF-IR β-chain on HT29 cells.

FIGS. 6A-6C: In vivo activity of I-3466 in DU145 (FIG. 6A), SK-ES-1 (FIG. 6B), HT29 (FIG. 6C), A549 (FIG. 6D) and MCF-7 (FIG. 6E) xenograft tumour models.

FIG. 7: Comparison of the amino acid sequences of the variable regions of the light chains (VL) of mouse I-3466 (SEQ ID No. 7) and of humanized by CDR-grafting I-3466 (SEQ ID No. 20).

The symbol * (asterisk) indicates important residues for the maintenance of CDR loop conformation and the symbol # (sharp) indicates conserved residues found at the VL/VH interface.

FIG. 8: Comparison of the amino acid sequences of the variable regions of the heavy chains (VH) of mouse I-3466 (SEQ ID No. 8) and of humanized by CDR-grafting I-3466 (SEQ ID No. 21).

The symbol * (asterisk) indicates important residues for the maintenance of CDR loop conformation and the symbol # (sharp) indicates conserved residues found at the VL/VH interface.

Figure 9:
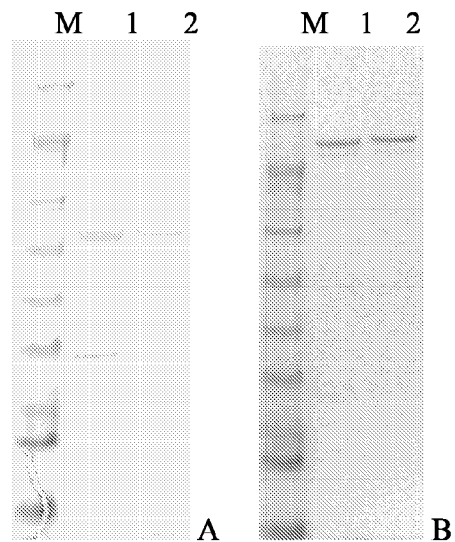

FIG. 9: SDS-PAGE analysis of purified I-3466 antibodies. The legend is the following:
M: Marker,
Lane 1: I-3466 humanized variable region,
Lane 2: I-3466 mouse variable region,
Panel A: Reducing SDS-PAGE,
Panel B: Non-reducing SDS-PAGE.

The constant regions for both mouse and humanized 3466 are human.

Figure 10:
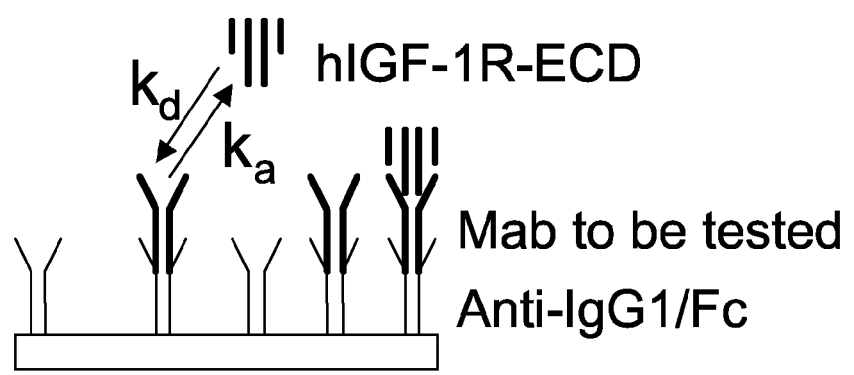

FIG. 10: Schematic representation of the biosensor capturing assay.

A human IgG1 Mab directed against the constant Fc portion, was covalently attached onto a CM5 sensor surface. A limited amount of Mab to be tested was immobilized and used to capture the analyte hIGF-IR-ECD. The binding of Mab to the analyte is characterized by the association and dissociation rate constants $k_a$ and $k_d$, respectively. The equilibrium dissociation constant (KD) is calculated by the ratio between dissociation and association rate constants.

Figure 11:
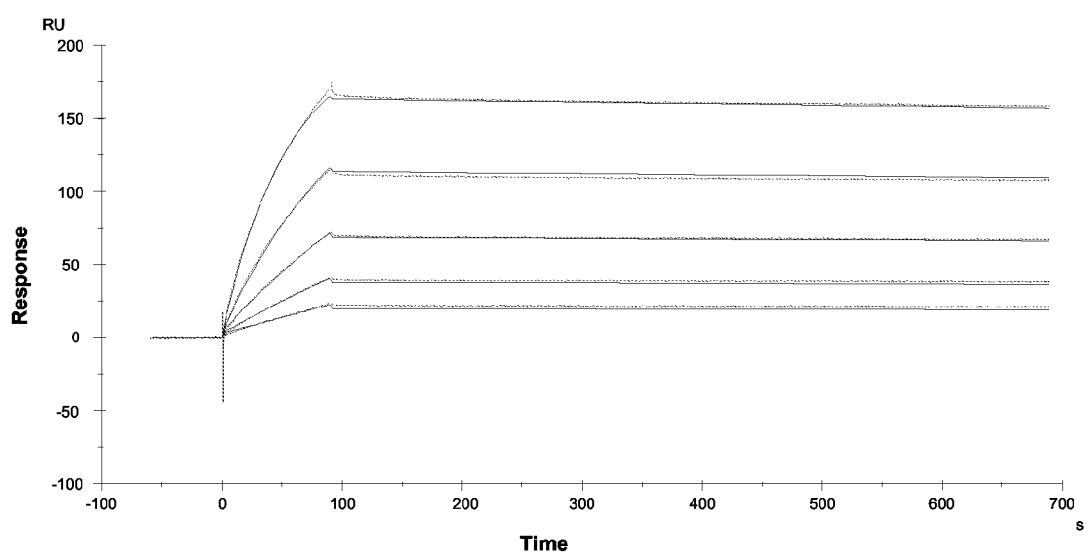

FIG. 11: Sensorgram of the association and dissociation phase of IgG1 humanized I-3466/hIGF-IR-ECD complexes for five different concentrations of hIGF-IR-ECD.

EXAMPLE 1

Generation and Selection of the Murine Monoclonal Antibody (MAb)

With the aim of generating MAb specifically directed against IGF-IR and not recognizing the IR, a protocol comprising 6 screening stages was performed.

It consisted in:
immunizing mice with human recombinant IGF-IR, in order to generate hybridomas,
screening the culture supernatants by ELISA on the recombinant protein which served for immunization,
testing all the supernatants of hybridomas positive by ELISA on the native receptor overexpressed on the surface of MCF-7 tumor cells,
performing binding experiments to select antibodies recognizing specifically IGF-IR,
verifying that the antibodies selected at this stage were capable of inhibiting in vitro the induced IGF1 proliferation of the MCF-7 cells,
ensuring the in vivo activity, in nude mice, of the candidate retained in terms of impact on the growth of the tumor MCF-7.

All of these different stages and results obtained will be briefly described below in example 1.

For the immunization stage, mice were injected twice, by the subcutaneous route, with 8 μg of recombinant IGF-IR. Three days before the fusion of spleen cells with the cells of the murine myeloma Sp2OAg14, the mice recieved by an intravenous injection of 3 μg of the recombinant receptor. Fourteen days after the fusion, the supernatants of hybridomas were screened by ELISA, on plates sensitized by recombinant IGF-IR. The hybridomas whose supernatants were found positive were conserved and amplified before being tested by FACScan analysis so as to verify that the antibodies produced were likewise capable of recognizing native IGF-IR.

EXAMPLE 2

Inhibition of [$^{125}$I]-IGF1 and [$^{125}$I]-IGF2 Binding to Human IGF-1 Receptor Preparation of Membrane Lysate NIH 3T3 cells stably transfected with the human IGF-IR cDNA were grown in DMEM supplemented with 10% of fetal calf serum. After detachment by scraping, serum-starved cells were further collected by centrifugation. The cell pellet was washed with phosphate buffered saline and resuspended in lysis buffer: 10 mM Tris-HCl pH 7.5 buffer containing protease inhibitors. Approximately 1 ml of buffer was added to 25.10$^6$ cells. Cells were further lysed by 3 freeze-thawing cycles followed by 30 strokes of a Potter homogeniser at 1,900 rpm. After sonication, nuclei and large cell fragments were discarded by centrifugation at 1,000 g for 15 min at +4° C. Total cell membranes were obtained by centrifugation at 105,000 g for 1 h at +4° C. The membrane pellet was washed in lysis buffer and centrifuged at 105,000 g for 1 h at +4° C. The final pellet was resuspended in 50 mM Tris-HCl buffer containing 150 mM NaCl, 0.5% IGEPAL, 0.5% Triton X-100, 0.25% sodium deoxycholate and protease inhibitors, and stirred overnight at +4° C. Insoluble material was separated from the soluble extract containing hIGF-IR by centrifugation at 10,000 g for 10 min at +4° C. Membrane lysates were analyzed for protein concentration by the bicinchoninic assay and for IGF-IR by western blot.

[$^{125}$I]-IGF1 and [$^{125}$I]-IGF2 Binding Assays

The commercially available monoclonal antibody 17-69 (Neomarkers, Fremont, Calif., USA), which has been described to recognize the IGF-IR alpha-subunit, was first coated on Protein A FlashPlate® 96-well microplates (Perkin Elmer, Boston, Mass., USA) to immobilize IGF-IR. Two hundred µl of a 20 µg/ml antibody solution in PBS were added to each well and incubated overnight at +4° C. The buffer containing residual 17-69 not attached to protein A was removed by aspiration. Two hundred µl of the membrane lysate at 100 µg/ml were further added and incubated for 2 h at room temperature to immobilize IGF-IR. Non captured proteins were removed by aspiration. For competition assays, binding of [$^{125}$I]-IGF1 (Perkin Elmer, Boston, Mass., USA) or [$^{125}$I]-IGF2 (Amersham Biosciences, Saclay, France) at 100 pM to immobilized IGF-IR was measured in the presence of varying concentrations of the monoclonal antibody I-3466 or the ligands IGF1, IGF2 and insulin (Sigma, Saint-Quentin Fallavier, France) ranging from 1 pM to 1 µM in binding buffer containing 50 mM Hepes pH 7.6, 150 mM NaCl, 0.05% Tween 20, 1% bovine serum albumin and 1 mM PMSF. The plates were incubated at room temperature for 2 h, then counted on a Packard Top Count Microplate Scintillation Counter. Non specific binding was determined in the presence of 1 µM of IGF1. The monoclonal antibody 9G4, which is not directed at hIGF-IR but specifically recognizes an *E. coli* protein, was used as mouse IgG1 isotype control.

Results

Percent of specific [$^{125}$I]-IGF1 and [$^{125}$I]-IGF2 binding was plotted as a function of ligand concentration on semilog graphs. Concentrations of the various inhibitors required to inhibit the radioligand binding by 50% (IC$_{50}$) were determined graphically from the sigmoid competition curves obtained (FIGS. 1 and 2).

Both IGF1 and IGF2 ligands efficiently displaced [$^{125}$I]-IGF1 binding to immobilized hIGF-IR, whereas insulin and the isotype control antibody 9G4 were unable to inhibit [$^{125}$I]-IGF1 binding at concentration lower than 500 nM (FIG. 1). The monoclonal antibody I-3466 was able to inhibit the binding of [$^{125}$I]-IGF1 with an IC$_{50}$ of 0.021 nM (FIG. 1), which is 30-fold lower than the IC$_{50}$ determined for non radio labeled IGF 1.

Moreover, the antibody I-3466 also exhibited a strong binding inhibition activity of [$^{125}$I]-IGF2 for immobilized hIGF-IR (FIG. 2). In this case, the IC$_{50}$ value deduced from the competition curve was around 0.1 nM. This IGF2 blocking activity of I-3466 was similar to the inhibitory activity induced by IGF2 (IC$_{50}$=0.06 nM). This was slightly lower than the inhibitory activity of IGF1 (IC$_{50}$=0.02 nM) and significantly greater than that of insulin (IC$_{50}$~200 nM). As expected, the control antibody 9G4 did not show any IGF2 blocking activity.

EXAMPLE 3

In Vitro Effect of the I-3466 Antibody on Either IGF1 or IGF2-Induced MCF-7 Growth As indicated above, IGF-IR is overexpressed by numerous tumors but it has furthermore been described that in a significant number of breast and colon cancers, the proliferation signal is given to this receptor via IGF2 (sometimes written IGF-2, IGF-II or IGFII). It is therefore essential to ensure that the MAb I-3466 is likewise capable of inhibiting both the IGF1 and the IGF2-induced growth on MCF-7 cells in vitro. In order to do this, cells were plated into 96-well plates at a density of 5×10$^4$ cells/well in 200 µl of serum free medium (phenol red free-RPMI medium plus 1% L-Glutamine). Twenty four hours after plating, either IGF1 at a final concentration of 50 µg/ml (6.6 nM) or IGF-2 (final concentration of 100 ng/ml (13.2 nM)) was added to MCF-7 cells either in presence or in absence of I-3466 or a murin non neutralizing anti-IGF-IR antibody (7G3) used as an isotype control for nearly 52 additional hours.

Antibodies were tested at final concentrations ranging from 10 µg/ml (66 nM) and 0.0097 µg/ml (0.065 nM). Then cells were pulsed with 0.25 µCi of [$^3$H]thymidine for 16 hours and the magnitude of [$^3$H]thymidine incorporated in DNA was quantified by liquid scintillation counting. Both IGF-1 and IGF-2 significantly stimulate MCF-7 cell growth (Table 2).

No significant inhibition was observed when cells were treated with increasing doses of the isotype control antibody.

In contrast, when cells were incubated with increasing doses of the I-3466 antibody a significant dose dependant inhibition of both IGF1 (90%) and IGF2 (84%)-induced proliferation was observed with IC$_{50}$s of 0.7 nM and 0.5 nM respectively (Table 2 and FIGS. 3A-3B).

TABLE 2

In vitro effect of the I-3466 antibody on either IGF1 (A)- or IGF2 (B)-induced MCF-7 growth

| A | | B | |
|---|---|---|---|
| | cpm | | cpm |
| Cells alone | 1449 | Cells alone | 1877 |
| IGF1 50 ng/ml | 67356 | IGF2 100 ng/ml | 39541 |
| 7G3 0.0097 µg/ml + IGF1 | 72144 | 7G3 0.0097 µg/ml + IGF2 | 60902 |
| 7G3 0.0195 µg/ml + IGF1 | 63200 | 7G3 0.0195 µg/ml + IGF2 | 67617 |
| 7G3 0.039 µg/ml + IGF1 | 53391 | 7G3 0.039 µg/ml + IGF2 | 56688 |
| 7G3 0.078 µg/ml + IGF1 | 56523 | 7G3 0.078 µg/ml + IGF2 | 60787 |
| 7G3 0.156 µg/ml + IGF1 | 46147 | 7G3 0.156 µg/ml + IGF2 | 49111 |
| 7G3 0.312 µg/ml + IGF1 | 54582 | 7G3 0.612 µg/ml + IGF2 | 48619 |
| 7G3 0.625 µg/ml + IGF1 | 53000 | 7G3 0.625 µg/ml + IGF2 | 51277 |
| 7G3 1.25 µg/ml + IGF1 | 58341 | 7G3 1.25 µg/ml + IGF2 | 54369 |
| 7G3 2.5 µg/ml + IGF1 | 51107 | 7G3 2.5 µg/ml + IGF2 | 53564 |
| 7G3 5 µg/ml + IGF1 | 45938 | 7G3 5 µg/ml + IGF2 | 54188 |
| 7G3 10 µg/ml + IGF1 | 34391 | 7G3 10 µg/ml + IGF2 | 55125 |
| I-3466 0.0097 µg/ml + IGF1 | 63047 | I-3466 0.0097 µg/ml + IGF2 | 45066 |
| I-3466 0.0195 µg/ml + IGF1 | 56376 | I-3466 0.0195 µg/ml + IGF2 | 43890 |
| I-3466 0.039 µg/ml + IGF1 | 48403 | I-3466 0.039 µg/ml + IGF2 | 31063 |
| I-3466 0.078 µg/ml + IGF1 | 38986 | I-3466 0.078 µg/ml + IGF2 | 27852 |
| I-3466 0.156 µg/ml + IGF1 | 33595 | I-3466 0.156 µg/ml + IGF2 | 18115 |
| I-3466 0.312 µg/ml + IGF1 | 27966 | I-3466 0.312 µg/ml + IGF2 | 13708 |
| I-3466 0.625 µg/ml + IGF1 | 17166 | I-3466 0.625 µg/ml + IGF2 | 9400 |
| I-3466 1.25 µg/ml + IGF1 | 10791 | I-3466 1.25 µg/ml + IGF2 | 7465 |
| I-3466 2.5 µg/ml + IGF1 | 8281 | I-3466 2.5 µg/ml + IGF2 | 6210 |
| I-3466 5 µg/ml + IGF1 | 5721 | I-3466 5 µg/ml + IGF2 | 6128 |
| I-3466 10 µg/ml + IGF1 | 6823 | I-3466 10 µg/ml + IGF2 | 7427 |

EXAMPLE 4

I-3466 Inhibit Both the IGF1- and IGF2-Induced Phosphorylation of the IGF-IR β-Chain Either MCF7 or HT29 cells were cultured for 24 hours at $5.10^4$ cells/cm$^2$ (75 cm$^2$ plates, COSTAR) in 20 ml of RPMI without phenol red, mixed with 5 mM of glutamine, penicillin/streptomycin (respectively 100 U/100 μg/ml) and 10% of fetal calf serum. After three washes in PBS, cells were incubated for 12 hours in phenol red-free medium (RPMI) without fetal calf serum and mixed with 5 mM of glutamine, penicillin/streptomycin, bovine serum albumin at 0.5 μg/ml (Sigma A-8022) and transferrin at 5 μg/ml (Sigma T8158).

For activation, cells were first incubated at 37° C. for 15 minutes with blocking antibodies (10 μg/ml) to be tested and then either IGF1 or IGF2 was added for two additional minutes. The reaction was stopped by aspiration of the incubation medium and the plates were laid on ice. Cells were solubilized by addition of 0.5 ml of lysis buffer (50 mM tris-HCl pH 7.5, 150 mM NaCl, 1% Nonidet P40, 0.5% sodium deoxycholate), mixed with protease inhibitors (1 tablet per 50 ml, Boehringer Ref.: 1697 498), and phosphatase inhibitors (Calbiochem Ref.: 524625 (1/100)). Cells were scraped off and the suspension was recovered and placed on a shaker at 4° C. for 1.5 hours. The solutions were centrifuged at 12,000 rpm for ten minutes (4° C.) and the protein concentrations of the supernatants were quantified by BCA.

500 μg of proteins of the cell lysate were mixed with the anti-IGF-IR (Santa cruz Ref.: sc-713) for immunoprecipitation and incubated on the shaker at 4° C. for 1.5 hours. The immunoprecipitates were recovered by addition of protein A-agarose (Boehringer Ref.: 1 134 515) and incubated all night on the shaker at 4° C. The agarose beads were washed twice with 1 ml of lysis buffer, twice with a wash buffer 1 (50 mM tris-HCl pH 7.5; 500 mM NaCl; 0.1% Nonidet P40; 0.05% sodium deoxycholate (Boehringer 1 332 597), mixed with protease inhibitors and phosphatase inhibitors) and once with a wash buffer 2 (50 mM tris-HCl; 0.1% Nonidet P40; 0.05% sodium deoxycholate (Boehringer Ref.: 1 332 597), mixed with protease inhibitors and phosphatase inhibitors 1/100). The immunoprecipitates were resuspended in a Laemmli buffer, heated to 100° C. for 5 minutes. The supernatants were analyzed by electrophoresis on polyacrylamide SDS gel (8% Novex EC6015). The proteins were transferred to a nitrocellulose membrane followed by either an immunoblot with anti-phosphotyrosine antibodies conjugated to HRP (BD transduction Labs PY20) or beta anti-chain of IGF-IR (Santa Cruz Ref.: sc 713) followed by an anti-rabbit antibody conjugated to HRP. The imprints were revealed by chemiluminescence (Amersham RPN 2209) followed by autoradiography on Kodak X-mat AR films.

FIGS. 4A and 4B represent MCF-7 cells nonstimulated (lanes 1, panel A and B) or stimulated either with 50 ng/ml IGF 1 alone (lane 2, panel A) or 100 ng/ml IGF2 (lanes 2, panel B). As expected no basal stimulation of IGF-IR was observed in MCF-7 cells while a significant phosphorylation of the IGF-IR β-chain was observed when MCF-7 cells were incubated either with IGF1 or IGF2. No stimulation was observed when cells were treated with an IgG1 isotype control (lanes 3, panel A and B) or with the I-3466 antibody alone (lanes 4, panel A and B) demonstrating that I-3466 displayed no agonistic effect on the IGF-IR. When I-3466 was added either with IGF1 or IGF2, a complete inhibition of the ligand-induced phosphorylation was observed (lanes 5, panel A and B). The 9G4 antibody used as isotype control was without any effect on either IGF1 or IGF2-induced phosphorylation (lanes 6, panel A and B).

The same inhibitory activity of I-3466 was observed on HT29 cells stimulated either with IGF1 or IGF2 (FIGS. 5A and 5B). These results are in agreement with the ones described in example 2 showing that I-3466 is able to displace both IGF1 and IGF2 from IGF-IR.

EXAMPLE 5

Internalization and Degradation Studies of the IGF-IR

Internalization and degradation studies were analyzed by FACS analysis. Internalization studies were performed using a murine biotinylated anti-IGF-IR monoclonal antibody (Mab) thereafter described as 12B1 Mab and binding to an epitope different from the one recognized by I-3466 antibody. The 9G4 Mab, was introduced as an isotype control. Both antibodies were generated in our laboratory. Confluent MCF-7 cells were trypsinized and $1\times10^6$ cells from each cellular suspension was plated in 96-well plates in FACS buffer. Plates were incubated, 4 hours at 37° C. with either IGF1 (50 ng/ml) or with 30 μg/ml of I-3466, 9G4, mIgG1.

Cells incubated with FACS buffer alone were used to determine the basal level of expression of the IGF-IR.

Then cells were washed twice and 20 μg/ml of biotinylated-12B1 MAb were added to the plate. After 30 min of incubation at 4° C. to avoid receptor internalization, cells were washed 3 times at 4° C. and stained by addition of a streptavidin Alexa Fluor® 488-conjugate (Molecular Probes Europe BV, Leiden, Netherlands). For degradation experiments an additional step of cell permeabilization was added befor staining cells with biotinylated-12B1 and streptavidin Alexa Fluor® 488-conjugate.

Table 3 showed that I-3466 causes a down regulation of the IGF-IR on both MCF-7 and 11T29 cells after a 4 hours incubation period. No down regulation was observed when cells were incubated with the 9G4 Mab, used as an isotype control.

TABLE 3

Internalization/degradation experiments of IGF-IR by the I-3466 antibody

| cell line ID | Tested Mab | MFI 12B1-mIgG1 | |
|---|---|---|---|
| A - Internalization experiment ||||
| | | | % internalization |
| MCF-7 | PBS | 247 | |
| | 9G4 | 226 | |
| | I-3466 | 31 | 86 |
| HT29 | PBS | 69 | |
| | 9G4 | 63 | |
| | I-3466 | 42 | 33 |
| B - Degradation experiment ||||
| | | | % degradation |
| MCF-7 | PBS | 112 | |
| | 9G4 | 105 | |
| | I-3466 | 37 | 65 |
| HT29 | PBS | 34 | |
| | 9G4 | 48 | |
| | I-3466 | 23 | 52 |

EXAMPLE 6

Anti-Tumor Effects of I-3466 Mab on DU145, SK-ES-1, HT29, A549 and MCF-7 Xenograft Tumor Models To explore the activity of I-3466 antibody on in vivo tumor growth, five xenograft tumor models have been used: the androgen independent DU145 prostate cancer, the osteosarcoma SK-ES-1, the colon cancer HT29, the non-small cell lung cancer A549 and the breast cancer MCF-7. For that purpose, female athymic 6-8-week-old nude mice were injected subcutaneously with $2.10^6$, $5.10^7$, $5.10^6$, $10.10^6$ and $5.10^6$ for DU-145, SK-ES-1, HT29, A549 and MCF-7 respectively. For DU145 and SK-ES-1 mice were treated 24 hours after cell injection with 200 µg of non purified antibody. Treatment was repeated twice a week. Concerning HT29, the treatment started when tumours reach a volume comprised between 49 and 59 mm³ and mice were injected i.p., 3 times a week, with 0.5 mg of purified antibody.

For A549, initial tumor volumes were comprised between 38 to 43 mm³ and for the MCF-7 experiments, they were comprised between 42 and 59 mm³ at the beginning of the treatment. Tumor volume was evaluated once or twice a week and calculated by the following formula: $\pi/6 \times length \times width \times height$.

FIGS. 6A-6E showed results partly performed with non purified antibody indicating that I-3466 is able to significantly inhibit in vivo tumour growth of the 5 tested cell lines.

EXAMPLE 7

Cloning, Production and Characterization of the Humanized I-3466 IgG1 Antibody Chemically synthesized variable regions for light and heavy chains of the humanized antibody I-3466 were PCR amplified and cloned into antibody expression vectors carrying human light chain kappa and heavy chain IgG1 constant regions, respectively. The PCR primers contain 36 nucleotides with 15 nucleotides for In-Fusion annealing with the vector overlapping cloning region and 21 nucleotides for annealing with the variable regions. The exact nucleotide sequences are shown below:
for light chain variable region cloning:

```
IF-Humanized I-3466-LCK-F
                                    (SEQ ID No. 21)
[5'-ACAGATGCCAGATGCGACATTGTGATGACCCAGTCC], IF-Humanized I-3466-LCK-R
                                    (SEQ ID No. 22)
[5'-TGCAGCCACCGTACGCTTGATCTCCACCTTGGTGCC],
``` for heavy chain variable region cloning:

```
IF-Humanized I-3466-HCG1-F
                                    (SEQ ID No. 23)
[5'-ACAGGTGTCCACTCGGAGGTGCAGCTGGTGGAGTCT], IF-Humanized I-3466-HCG1-R
                                    (SEQ ID No. 24)
[5'-GCCCTTGGTGGATGCGGAGGAGACTGTCACCAGGGT].
```

The vectors were linearized with BmtI and FspI digestion. The In-Fusion reaction was carried out according to vendor's recommended protocol. The resulting clones were confirmed by sequencing. Human embryonic kidney 293 cells were transfected using light and heavy chain plasmid DNAs. Medium containing secreted antibody was harvested and concentrated. The antibody was affinity purified using protein A/G column and concentrated and dialyzed in PBS. The protein concentration was determined by OD280 nm and the purity was analyzed by reducing and non-reducing SDS-PAGE (FIG. 9).

EXAMPLE 8

BIACore Analysis of Humanized I-3466 IgG1 antibody

Equipment and Materials

BIAcore T100 instrument, CM5 biosensor chips, HBS-EP buffer, acetate buffer (pH 5), Glycine-HCl buffer (pH 1.5), amine coupling kit were from BIAcore (Upsala, Sweden). Anti-human IgG Fc was from Jackson ImmunoResearch Laboratories Inc. (West Grove, USA), soluble human insulin-like growth factor-1 receptor (hIGF-IR) extra-cellular domain (ECD) was from R&D Systems (Minneapolis, USA).

Biacore Assay

All experiments were performed at 25° C. at a flow rate of 40 µl/min. To prepare a BIAcore assay (see FIG. 10), an anti-human IgG-Fc antibody (50 µg/ml in acetate buffer, pH 5) was immobilized onto a carboxymethyl dextran sensorchip (CM5) using amine coupling procedures as described by the manufacturer. 11042 and 11111 resonance units (RU) of anti-IgG Fc antibodies were linked respectively onto Flowcells (FC) 1 and 3. Purified Mabs to be tested were diluted at a concentration of 5 µg/ml in 0.5% P20, HBS-EP buffer and injected on FC3 to reach 500 to 1000 RU. FC1 was used as the reference cell. Specific signals correspond to the difference of signals obtained on FC2 versus FC1. The analyte (soluble hIGF-IR, apparent molecular weight 365 kDa) was injected during 90 sec at 5 different concentrations (100, 50, 25, 12.5 and 6.25 nM) in 0.5% P20, IIBS-EP buffer. These concentrations were prepared from stock solution in 0.5% P20, HBS-EP. The dissociation phase of the analyte was monitored over a 10 minutes period. Running buffer was also injected under the same conditions as a double reference. After each cycle (antibody+hIGF-IR injection), both Flowcells were regenerated by injecting 20 to 45 µl of Glycine-HCl buffer (pH 1.5). This regeneration is sufficient to eliminate all Mabs and Mabs/hIGF-IR complexes captured on the sensorchip.

Result

The binding of the Mab Humanized I-3466 to the analyte hIGF-IR-ECD was characterized by the association and dissociation rate constants $k_a$ and $k_d$, respectively. The equilibrium dissociation constant (KD) was calculated by the ratio between dissociation and association rate constants. Results are given in the following Table 4. The sensorgram corresponding to the different analyte concentrations is represented in the FIG. 11.

TABLE 4

| IGF-IR Abs | ka (1/Ms) | kd (1/s) | KD (M) |
|---|---|---|---|
| IgG1 HI3466 | 1.84E+05 | 6.29E−05 | 3.42E−10 |

The invention claimed is:

1. An isolated nucleic acid, selected from the group consisting of:
   a) a nucleic acid coding for an antibody that specifically binds insulin-like growth factor 1 receptor (IGF-1R), or an antigen binding fragment thereof, wherein the antibody or antigen binding fragment thereof comprises: (i) a heavy chain comprising three CDRs of sequence SEQ ID NOS: 2, 4 and 6, and (ii) a light chain comprising three CDRs of sequence SEQ ID NOS: 1, 3 and 5;
   b) a nucleic acid comprising three CDRs of sequence SEQ ID NOS: 9, 10 and 11, and/or three CDRs of sequence SEQ ID NOS: 12, 13 and 14;
   c) a nucleic acid comprising the light chain of sequence SEQ ID NO: 15 and/or the heavy chain of sequence SEQ ID NO: 16; and
   d) a nucleic acid comprising the light chain of sequence SEQ ID NO: 19 and/or the heavy chain of sequence SEQ ID NO: 20.

2. A vector comprising one or more of the nucleic acids of claim 1.

3. A host cell comprising the vector of claim 2.

4. A process for production of an antibody, or an antigen binding fragment thereof, which comprises:
   a) culturing in a medium and under appropriate culture conditions the cell of claim 3; and
   b) recovering the antibody, or the antigen binding fragment thereof from the culture medium or said cultured cell.

5. The isolated nucleic acid of claim 1, which is a complementary nucleic acid of the nucleic acid of a).

* * * * *

SEQUENCE LISTING

<160> NUMBER OF SEQ ID NOS: 24

<210> SEQ ID NO 1
<211> LENGTH: 17
<212> TYPE: PRT
<213> ORGANISM: mus musculus

<400> SEQUENCE: 1

Lys Ser Ser Gln Ser Leu Leu Asp Ser Arg Thr Arg Lys Asn Tyr Leu
1               5                   10                  15

Ala

<210> SEQ ID NO 2
<211> LENGTH: 6
<212> TYPE: PRT
<213> ORGANISM: mus musculus

<400> SEQUENCE: 2

Asn Asn Tyr Ile Met Ser
1               5

<210> SEQ ID NO 3
<211> LENGTH: 7
<212> TYPE: PRT
<213> ORGANISM: mus musculus

<400> SEQUENCE: 3

Trp Ala Ser Thr Arg Glu Ser
1               5

<210> SEQ ID NO 4
<211> LENGTH: 17
<212> TYPE: PRT
<213> ORGANISM: mus musculus

<400> SEQUENCE: 4

Thr Ile Ser Gly Gly Gly Ser Tyr Thr Phe Tyr Pro Asp Ser Val Lys
1               5                   10                  15

Gly

<210> SEQ ID NO 5
<211> LENGTH: 8
<212> TYPE: PRT
<213> ORGANISM: mus musculus

<400> SEQUENCE: 5

Lys Gln Ser Tyr Asn Leu Phe Thr
1               5

<210> SEQ ID NO 6
<211> LENGTH: 20
<212> TYPE: PRT
<213> ORGANISM: mus musculus

<400> SEQUENCE: 6

Asn Gln Leu Leu Thr Gly Met Ile Asn Pro Leu Thr Thr Pro Arg Ala
1               5                   10                  15

Trp Phe Thr Tyr
            20

```
<210> SEQ ID NO 7
<211> LENGTH: 112
<212> TYPE: PRT
<213> ORGANISM: mus musculus

<400> SEQUENCE: 7

Asp Ile Val Met Ser Gln Ser Pro Ser Ser Leu Ala Val Ser Ala Gly
1               5                   10                  15

Glu Lys Val Thr Met Asn Cys Lys Ser Ser Gln Ser Leu Leu Asp Ser
            20                  25                  30

Arg Thr Arg Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Lys Gln
                85                  90                  95

Ser Tyr Asn Leu Phe Thr Phe Gly Gly Thr Lys Leu Glu Ile Lys
            100                 105                 110

<210> SEQ ID NO 8
<211> LENGTH: 129
<212> TYPE: PRT
<213> ORGANISM: mus musculus

<400> SEQUENCE: 8

Glu Val Met Leu Val Glu Ser Gly Gly Asp Leu Val Lys Pro Gly Gly
1               5                   10                  15

Ser Leu Lys Leu Ser Cys Ala Ala Ser Gly Phe Thr Phe Asn Asn Tyr
            20                  25                  30

Ile Met Ser Trp Val Arg Gln Thr Pro Glu Lys Arg Leu Glu Trp Val
        35                  40                  45

Ala Thr Ile Ser Gly Gly Gly Ser Tyr Thr Phe Tyr Pro Asp Ser Val
    50                  55                  60

Lys Gly Arg Phe Ser Ile Ser Arg Asp Asn Ala Lys Asn Thr Leu Tyr
65                  70                  75                  80

Leu Gln Met Ser Ser Leu Arg Ser Glu Asp Thr Ala Met Tyr Phe Cys
                85                  90                  95

Thr Arg Asn Gln Leu Leu Thr Gly Met Ile Asn Pro Leu Thr Thr Pro
            100                 105                 110

Arg Ala Trp Phe Thr Tyr Trp Gly Gln Gly Thr Leu Val Thr Val Ser
        115                 120                 125

Ala

<210> SEQ ID NO 9
<211> LENGTH: 51
<212> TYPE: DNA
<213> ORGANISM: mus musculus

<400> SEQUENCE: 9
aaatccagtc agagtctact cgacagtaga acccgaaaga actacttggc t          51

<210> SEQ ID NO 10
<211> LENGTH: 18
<212> TYPE: DNA
<213> ORGANISM: mus musculus
```

<400> SEQUENCE: 10
aataactata tcatgtct                                           18

<210> SEQ ID NO 11
<211> LENGTH: 21
<212> TYPE: DNA
<213> ORGANISM: mus musculus

<400> SEQUENCE: 11
tgggcatcca ctagggaatc t                                       21

<210> SEQ ID NO 12
<211> LENGTH: 51
<212> TYPE: DNA
<213> ORGANISM: mus musculus

<400> SEQUENCE: 12
accattagtg gtggtggtag ttataccttc tatccagaca gtgtgaaggg a       51

<210> SEQ ID NO 13
<211> LENGTH: 24
<212> TYPE: DNA
<213> ORGANISM: mus musculus

<400> SEQUENCE: 13
aagcaatctt ataatctgtt cacg                                    24

<210> SEQ ID NO 14
<211> LENGTH: 60
<212> TYPE: DNA
<213> ORGANISM: mus musculus

<400> SEQUENCE: 14
aatcaattac ttactgggat gatcaatccc ctgactacgc ctagagcctg gtttacttac    60

<210> SEQ ID NO 15
<211> LENGTH: 336
<212> TYPE: DNA
<213> ORGANISM: mus musculus

<400> SEQUENCE: 15
gacattgtga tgtcacagtc tccatcctcc ctggctgtgt cagcaggaga gaaggtcact    60
atgaactgca aatccagtca gagtctactc gacagtagaa cccgaaagaa ctacttggct   120
tggtaccagc agaagccagg acagtctcct aaactgctga tctactgggc atccactagg   180
gaatctgggg tccctgatcg cttcacaggc agtggatctg ggacagattt cactctcacc   240
atcagcagtg tgcaggctga agacctggca gtttattact gcaagcaatc ttataatctg   300
ttcacgttcg gagggggac caagctggaa ataaaa                             336

<210> SEQ ID NO 16
<211> LENGTH: 387
<212> TYPE: DNA
<213> ORGANISM: mus musculus

<400> SEQUENCE: 16
gaagtgatgc tggtggagtc tgggggagac ttagtgaagc ctggagggtc cctaaaactc    60
tcctgtgcag cctctggatt cactttcaat aactatatca tgtcttgggt tcgccagact   120
ccggagaaga ggctgagtg ggtcgcaacc attagtggtg gtgtagtta taccttctat    180 ccagacagtg tgaagggacg attctccatc tccagagaca atgccaagaa caccctgtat   240

```
ctgcaaatga gcagtctgag gtctgaggac acggccatgt atttctgtac aaggaatcaa    300
ttacttactg ggatgatcaa tcccctgact acgcctagag cctggtttac ttactggggc    360
caagggactc tggtcactgt ctctgca                                         387
```

<210> SEQ ID NO 17
<211> LENGTH: 112
<212> TYPE: PRT
<213> ORGANISM: Artificial sequence
<220> FEATURE:
<223> OTHER INFORMATION: Chemically synthesized humanized antibody, light chain

<400> SEQUENCE: 17

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asp Ser
            20                  25                  30

Arg Thr Arg Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Lys Gln
                85                  90                  95

Ser Tyr Asn Leu Phe Thr Phe Gly Gly Gly Thr Lys Val Glu Ile Lys
            100                 105                 110
```

<210> SEQ ID NO 18
<211> LENGTH: 129
<212> TYPE: PRT
<213> ORGANISM: Artificial sequence
<220> FEATURE:
<223> OTHER INFORMATION: Chemically synthesized humanized antibody, heavy chain

<400> SEQUENCE: 18

```
Glu Val Gln Leu Val Glu Ser Gly Gly Asp Leu Val Gln Pro Gly Gly
1               5                   10                  15

Ser Leu Arg Leu Ser Cys Ala Ala Ser Gly Phe Thr Phe Asn Asn Tyr
            20                  25                  30

Ile Met Ser Trp Val Arg Gln Ala Pro Gly Lys Gly Leu Glu Trp Val
        35                  40                  45

Ala Thr Ile Ser Gly Gly Gly Ser Tyr Thr Phe Tyr Pro Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Phe Cys
                85                  90                  95

Thr Arg Asn Gln Leu Leu Thr Gly Met Ile Asn Pro Leu Thr Thr Pro
            100                 105                 110

Arg Ala Trp Phe Thr Tyr Trp Gly Gln Gly Thr Leu Val Thr Val Ser
        115                 120                 125

Ser
```

```
<210> SEQ ID NO 19
<211> LENGTH: 336
<212> TYPE: DNA
<213> ORGANISM: Artificial sequence
<220> FEATURE:
<223> OTHER INFORMATION: Chemically synthesized humanized antibody,
      light chain

<400> SEQUENCE: 19
gacattgtga tgacccagtc ccctgactcc ctggctgtct ccctgggcga gcgggccacc      60
atcaactgca gtcctcccca gtccctgctg gactcccgga cccggaagaa ctacctggcc     120
tggtaccagc agaagcctgg ccagccccca aagctgctga tctactgggc ctccacccgg     180
gagtctggcg tgcctgaccg gttctctggc tctggctctg gcacagactt caccctgacc     240
atctcctccc tgcaggctga ggatgtggct gtctactact gcaagcagtc ctacaacctg     300
ttcacctttg gcggcggcac caaggtggag atcaag                               336

<210> SEQ ID NO 20
<211> LENGTH: 387
<212> TYPE: DNA
<213> ORGANISM: Artificial sequence
<220> FEATURE:
<223> OTHER INFORMATION: Chemically synthesized humanized antibody,
      heavy chain

<400> SEQUENCE: 20
gaggtgcagc tggtggagtc tggcggcgac ctggtgcagc ctggcggctc cctgcggctg      60
tcctgtgctg cctctggctt caccttcaac aactacatca gtcctgggt gcggcaggcc     120 cctggcaagg gcctggagtg ggtggccacc atctctggcg gcggctccta caccttctac     180
cctgactctg tgaagggccg gttcaccatc tcccgggaca actccaagaa caccctgtac     240
ctgcagatga actccctgcg ggctgaggac acagctgtct acttctgcac ccggaaccag     300
ctgctgacag gcatgatcaa ccccctgacc accccccggg cctggttcac ctactggggc     360
cagggcaccc tggtgacagt ctcctcc                                         387

<210> SEQ ID NO 21
<211> LENGTH: 36
<212> TYPE: DNA
<213> ORGANISM: Artificial sequence
<220> FEATURE:
<223> OTHER INFORMATION: Chemically synthesized IF-Humanized
      I-3466-LCK-F primer for humanized antibody I-3466 light chain
      amplification

<400> SEQUENCE: 21
acagatgcca gatgcgacat tgtgatgacc cagtcc                                36

<210> SEQ ID NO 22
<211> LENGTH: 36
<212> TYPE: DNA
<213> ORGANISM: Artificial sequence
<220> FEATURE:
<223> OTHER INFORMATION: Chemically synthesized IF-Humanized
      I-3466-LCK-R primer for humanized antibody I-3466 light chain
      amplification

<400> SEQUENCE: 22
tgcagccacc gtacgcttga tctccacctt ggtgcc                                36
```

```
<210> SEQ ID NO 23
<211> LENGTH: 36
<212> TYPE: DNA
<213> ORGANISM: Artificial sequence
<220> FEATURE:
<223> OTHER INFORMATION: Chemically synthesized IF-Humanized
      I-3466-HCG1-F primer for humanized antibody I-3466 heavy chain
      amplification

<400> SEQUENCE: 23
acaggtgtcc actcggaggt gcagctggtg gagtct                                 36

<210> SEQ ID NO 24
<211> LENGTH: 36
<212> TYPE: DNA
<213> ORGANISM: Artificial sequence
<220> FEATURE:
<223> OTHER INFORMATION: Chemically synthesized IF-Humanized
      I-3466-HCG1-R primer for humanized antibody I-3466 heavy chain
      amplification

<400> SEQUENCE: 24
gcccttggtg gatgcggagg agactgtcac cagggt                                 36
```